United States Patent

Lewis et al.

[11] Patent Number: 6,150,645
[45] Date of Patent: *Nov. 21, 2000

[54] RADIATION CONTROL SYSTEM

[75] Inventors: David Andrew Lewis, Carmel; Stanley Joseph Whitehair, Peekskill, both of N.Y.

[73] Assignee: International Business Machines Corporation, Armonk, N.Y.

[*] Notice: This patent is subject to a terminal disclaimer.

[21] Appl. No.: 09/129,505

[22] Filed: Aug. 5, 1998

Related U.S. Application Data

[63] Continuation-in-part of application No. 09/002,714, Jan. 5, 1998, and a continuation of application No. 09/002,719, Jan. 5, 1998, Pat. No. 6,054,696, which is a continuation-in-part of application No. 09/002,720, Jan. 5, 1998, Pat. No. 6,020,579, which is a continuation-in-part of application No. 09/002,849, Jan. 5, 1998, which is a continuation-in-part of application No. 09/003,016, Jan. 5, 1998, Pat. No. 6,020,580, which is a continuation-in-part of application No. 08/770,213, Dec. 19, 1996, Pat. No. 5,837,978, which is a continuation of application No. 07/782,841, Oct. 24, 1991, abandoned, which is a continuation-in-part of application No. 07/551,716, Jul. 11, 1990, Pat. No. 5,241,040.

[60] Provisional application No. 60/034,717, Jan. 6, 1997.

[51] Int. Cl.⁷ .................................................. H05B 6/66
[52] U.S. Cl. .......................... 219/715; 219/702; 219/705
[58] Field of Search ................................... 219/702–712, 219/719–720

[56] References Cited

U.S. PATENT DOCUMENTS 5,837,978   11/1998   Hatzakis, Jr. et al. .................. 219/702

Primary Examiner—Tu Ba Hoang
Attorney, Agent, or Firm—Thomas A. Beck

[57] ABSTRACT

A control system for a blind microwave radiation tool a workpiece is described. The controlled system automatically tunes the cavity containing the workpiece. The control system automatically controls the temperature of the workpiece according to a predetermined temperature versus time schedule. Control system automatically determines when the workpiece has reached a particular predetermined physical condition. To achieve these results the control system automatically monitors applied power, reflected power or current temperature and automatically controls the microwave cavity volume and shape and launch structure including antennae location, cavity short location, cavity diameter, coupling loop position, etc. in order to maintain the cavity in resonance and to determine when to exit without operator intervention. Control system can run on a small computer or an embedded controller and is useful for automatically curing polyamic acid to polyimide to a predetermined percent cure, processing preimpregnated glass cloth in a continuous manner which can be used in circuit boards and drying and partial curing of web-like materials automatically without operator intervention.

31 Claims, 15 Drawing Sheets

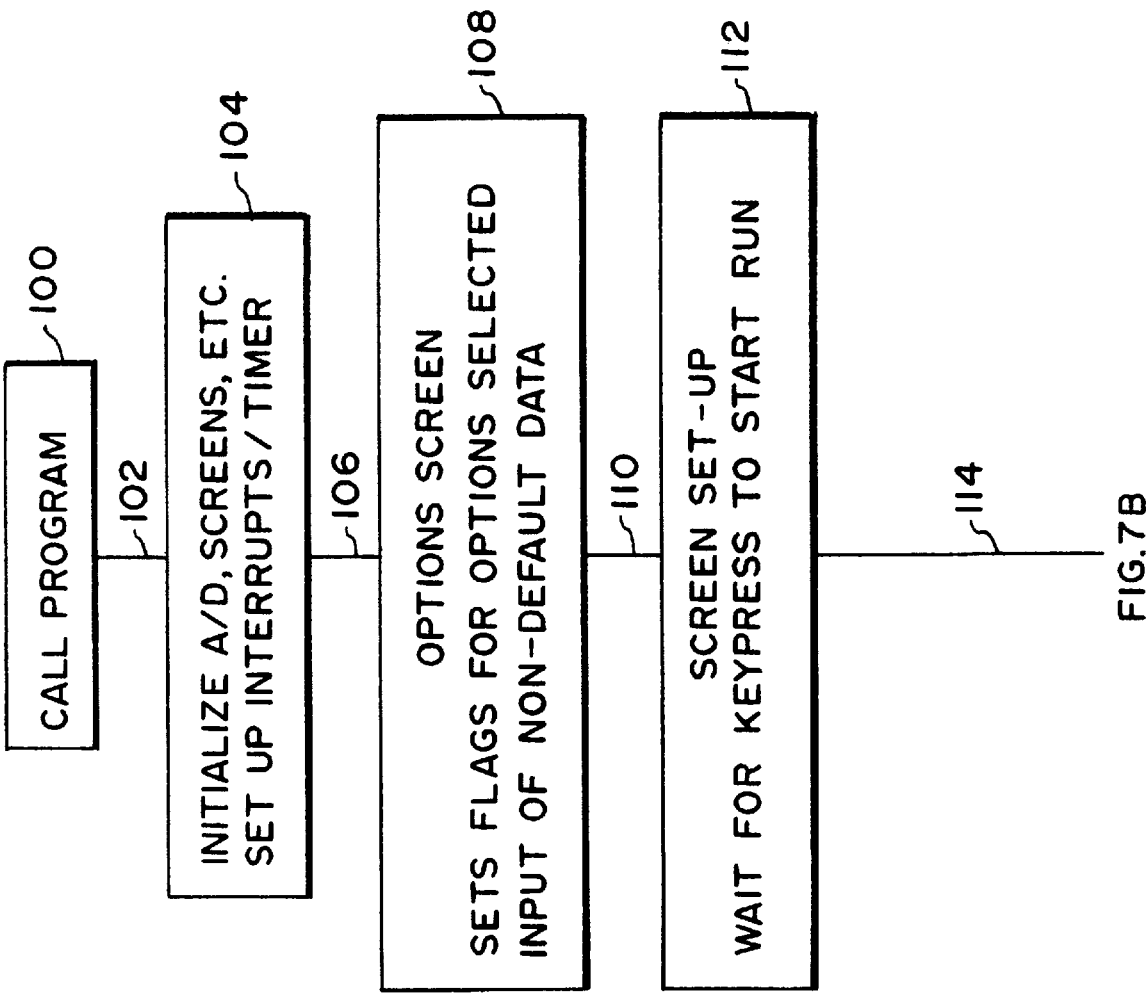

RADIATION CONTROL SYSTEM

This application is a continuation in part of U.S. application Ser. No. 09/002,714 filed on Jan. 5, 1998, which claim priority from U.S. Provisional Application Ser. No. 60/034, 717 filed on Jan. 6, 1997, the priority of both which is claimed and the teachings of both of which are incorporated herein by reference.

This application is a continuation in part of U.S. application Ser. No. 09/002,719 filed on Jan. 5, 1998, which claim priority from U.S. Provisional Application Ser. No. 60/034, 717 filed on Jan. 6, 1997, the priority of both which is claimed and the teachings of both of which are incorporated herein by reference.

This application is a continuation in part of U.S. application Ser. No. 09/002,720 filed on Jan. 5, 1998, now U.S. Pat. No. 6,020,579, which claim priority from U.S. Provisional Application Ser. No. 60/034,717 filed on Jan. 6, 1997, the priority of both which is claimed and the teachings of both of which are incorporated herein by reference.

This application is a continuation in part of U.S. application Ser. No. 09/002,849 filed on Jan. 5, 1998, which claim priority from U.S. Provisional Application Ser. No. 60/034, 717 filed on Jan. 6, 1997, the priority of both which is claimed and the teachings of both of which are incorporated herein by reference.

This application is a continuation in part of U.S. application Ser. No. 09/003,016 filed on Jan. 5, 1998, now U.S. Pat. No. 6,020,580, which claim priority from U.S. Provisional Application Ser. No. 60/034,717 filed on Jan. 6, 1997, the priority of both which is claimed and the teachings of both of which are incorporated herein by reference.

This application is a continuation-in-part of U.S. application Ser. No. 08/770,213 filed on Dec. 19, 1996, U.S. Pat. No. 5,837,978, which is a continuation of U.S. application Ser. No. 07/782,841 filed on Oct. 24, 1991 now abandoned which was a continuation in-part of U.S. application Ser. No. 07/551,716 filed on Jul. 11, 1990 issued as U.S. Pat. No. 5,241,040, the priority of all of which are claimed and the teachings of all of which are incorporated herein by reference.

DESCRIPTION

1. Field of the Invention

This invention relates to methods and systems for automated control of a radiation apparatus useful for the application of microwave radiation to physical processes and chemical reactions such as the preparation of polyinide polyimers from polyamic acid precursors dissolved in a solvent in which the solvent is volatilized by microwave radiation followed by imidization of the precursor by microwave radiation or the processing of a sheet-like material in a continuous manner. More particularly, the system is a computer control system. More particularly, the invention is directed to automated methods and systems for the application of microwave radiation to the precursor to automatically control the degree and rate of the process and to accurately determine the end point of or degree of processing by an in situ non-destructive testing method without operator intervention.

2. Background

In the fabrication of integrated circuits such as microcircuits, insulating layers are applied over the circuits or utilized in sandwich construction. These layers in some applications comprise polyimide films. The conventional polyimdes utilized in this respect are prepared from precursors that contain polyamic acid groups, polyamic ester groups or combinations thereof, the precursors in turn being prepared by the reaction of a dianhydride and diamine or a diester-diacid dichloride and diamine. The precursor that is produced is soluble in common organic solvents and when dissolved, can be applied to various substrates as a coating. After the substrate is coated the solvent is removed, usually by the application of heat to the coated substrate and with continued heating, the precursor is converted into a polyimide film with the evolution of water or alcohol as a product of the imidization reaction. The polyimide film obtained is not readily soluble in conventional solvents, is extremely strong, has excellent high temperature performance and can be made to adhere to most substrates, Because of the outstanding physical properties of polyimide resins, they have been widely used in many coating applications. One of the disadvantages of polyimides in all of the foregoing reactions is the cure time necessary to develop the ultimate mechanical properties which typically in thin film applications can be as high as ten to twelve hours.

As noted, the precursor is converted to the polyamide with the evolution of water or alcohol as a by-product of reaction. This imidization usually begins at about 150° C. whereas temperatures upwards of about 300° C. are required to complete the process which is sometimes referred to as dehydration and temperatures up to 400° C. are required to complete ordering processes for some polyimides.

In curing polyalic acid by this dehydration process to form the polyimide polymer, care must be exercised to ensure that even heating is effected throughout the cross-section of polyamic acid being converted, which is not always easy to achieve. For example, when films of polyamic acid are exposed to heat in conventional ovens, the film cures from the outer most surface inwardly and if the curing process proceeds at too high a rate, the outer surface of the film will be (i) cured significantly faster than the center, possibly resulting in void formation, or (ii) result in inferior mechanical properties such as reduced modulus, enhanced swelling, solvent uptake and GTE (coefficient of thermal expansion).

The prior art contains general disclosures regarding the use of wicrowave radiation to convert polyamic acid precursors to polyimides (U.S. Pat. Nos. 4,305,796 and 4,439, 381 to Gagliani et at. and U.S. Pat. No. 4,681,654 to Clementi et al.), however, as a practical matter greater than 50% conversion of the precursor to the polyimide has not been obtained.

It is believed that the problems encountered with microwave curing of polyamic acids to polyimides is due in large measure to the microwave device employed. The microwave apparatus conventionally utilized in this regard is similar in operation to a "ome microwave" i.e. a large, multimode chamber with one or more magnetrons coupling microwave radiation into the chamber. These systems typically operate at full power which is regulated bo turning it on or off, resulting in a form of "pulsed" radiation treatment. This apparatus has the disadvantages of non-uniform microwave fields which vary spatially with the movement and/or curing of the part and difficulty in providing controlled evaporation and curing rates, This can result in non-uniform curing on a small level, which in turn results in enhanced local stress in the film, since these materials shrink on curing. In addition, solvent evaporation is difficult to control resulting in poor film quality and it is difficult in such an arrangement to obtain sufficiently high electric field strengths (power density) to obtain full or substantially ull cure of the polymide. Gaghani et al. (supra) even describe the use of short bursts of microwave radiation in this regard.

Thus the prior art solution to the difficulties encountered with microwave curing was to employ the microwave process only for partial idization of polyamic acids to polyirides and subsequently heating the product obtained by means other than microwave radiation.

One of the other difficulties encountered in the prior art was that in situ test means were not available to determine the degree of imidization of the polyamic acid to polyimide. The product had to be removed from the imidizing reaction milieu and tested, either by wet analysis to determine the carboxylic acid groups in the product or by other test methods such as FTIR spectroscopy and the like.

These prior art methods employing microwave radiation also did not lend themselves to the precise control of the rate and degree of imidization of polyamic acid to polyimides over a range from partial imidization to substantially complete imidization in such a way as to optimize the mechanical properties of the imidized product.

There has also been no disclosure in the prior art of a method for exposing a polyimide precursor material to microwave radiation when the precursor has been placed on a substrate such as metal containing PC boards or various metal oxides such as alumina with metal wiring and pads and metal over Kapton (trademark) polyimide. It is usually assumed that arcing between the metal pads would result and damage the pads and dielectric material.

Additionally, microwave energy can be used to process other materials, such as preipregnated glass cloth, hereinafter called prepreg which is used to fabricate circuit boards, golf-club shafts, tennis rackets, etc.

This material is usually processed in a continuous, roll to roll manner in which the cloth passes through a heated zone which removed solvent or water from the web and partially cures the web (typically to about 25% conversion) to ensure that the prepreg is not tacky and will not stick to itself as it is rewound onto the take-up reel. The heated zone is currently hot air impinging on to the surface of the web, however, a microwave cavity or series of microwave applicators can be used to apply thermal eners to the moving web. Additionally, other web like materials can be processed In this manner, including paper products (in a ing press), textiles, etc to remove water from the web, dry inks, cure or partially cure coatings, etc.

The principle shortcoming is that cavites currently available can not provide a sufficiently uniform electric field across the width of the web resulting in poor uniformity of the product. In an apparatus of our invention, the work piece is held in a single mode microwave applicator, hereinafter referred to as a cavity, which is held in tune by minimizing the reflected microwave power as the physical properties of the work piece are changed as a result of the application of the radiation. Also, the temperature versus time progress of the workpiece is monitored and controlled according to a predetermined schedule by control of the radiation intensity.

In an apparatus of our invention the temperature versus time progress of a workpiece in a cavity is monitored and controlled according to a predetermined schedule by control of the radiation intensity while at the same time the same cavity is held in tune while at the same time the physical properties of the workpiece change as a result of the application of the radiation; by varying the location of the radiation source and cavity short with respect to the workpiece. The Q of the cavity is monitored and from the temperature—Q history it is determined when the workpiece has achieved a predetermined physical condition and when to stop the application of the radiation. Prior art methods manually control these types of procedures and at best have only partial automated control. The applicants have invented a complete automated control process.

In another apparatus of this invention, a workpiece is moved through a cavity or a plurality of cavities in series in a continuous manner. Temperature is monitored at each applicator and radiation intensity individually varied to the respective cavity to provide the desired temperature of the workpiece within the cavity. A predetermined temperature profile can be applied to the workpiece by providing the controlled temperature at each cavity. The Q of the cavity is monitored and from the temperature—Q history it is determined when the workpiece has achieved a predetermined physical condition to ensure the predetermined temperature—time profile is adequate to provide full processing and signal a process error if necessary.

U.S. Pat. No. 4,324,965 describes a method by which to automate the movement of a triple stub tuner in a waveguide wherein two stubs are moved at different rates simultaneously. In contradistinction, according to the present invention two axes are moved independently at independent speeds and to independent distances which provides a substantial enhancement.

U.S. Pat. No. 4,667,076 describes an apparatus for annealing a silicon wafer having elements to control temperature and gaseous environment. There is no need to tune the chamber since radiation emitting horn is used There is no teaching or suggestion of end point detection.

U.S. Pat. No. 4,760,228 describes microwave heating of a extradite from an extruder for which there is no built in control elements. Reflected power is minimized by the system design and is not controllable. Temperature is adjusted to a steady state by fixing the microwave power at a predetermined value.

It is an object of the present invention to provide a complete automation system to apply radiation to a workpiece and to automatically determine when to cease exposure to the radiation when the workpiece has reached a predetermined physical condition.

BRIEF DESCRIPTION OF THE DRAWINGS

FIG. 7 is an overall flow chart of the control system of the present invention which is used to automatically control the microwave apparatus according to the present invention to achieve a desired level of microwave application to the work piece according to the present invention.

FIG. 7A–7B are flow charts of the autotune subsystem of the system of FIG. 7.

SUMMARY OF THE INVENTION

Figure 1:
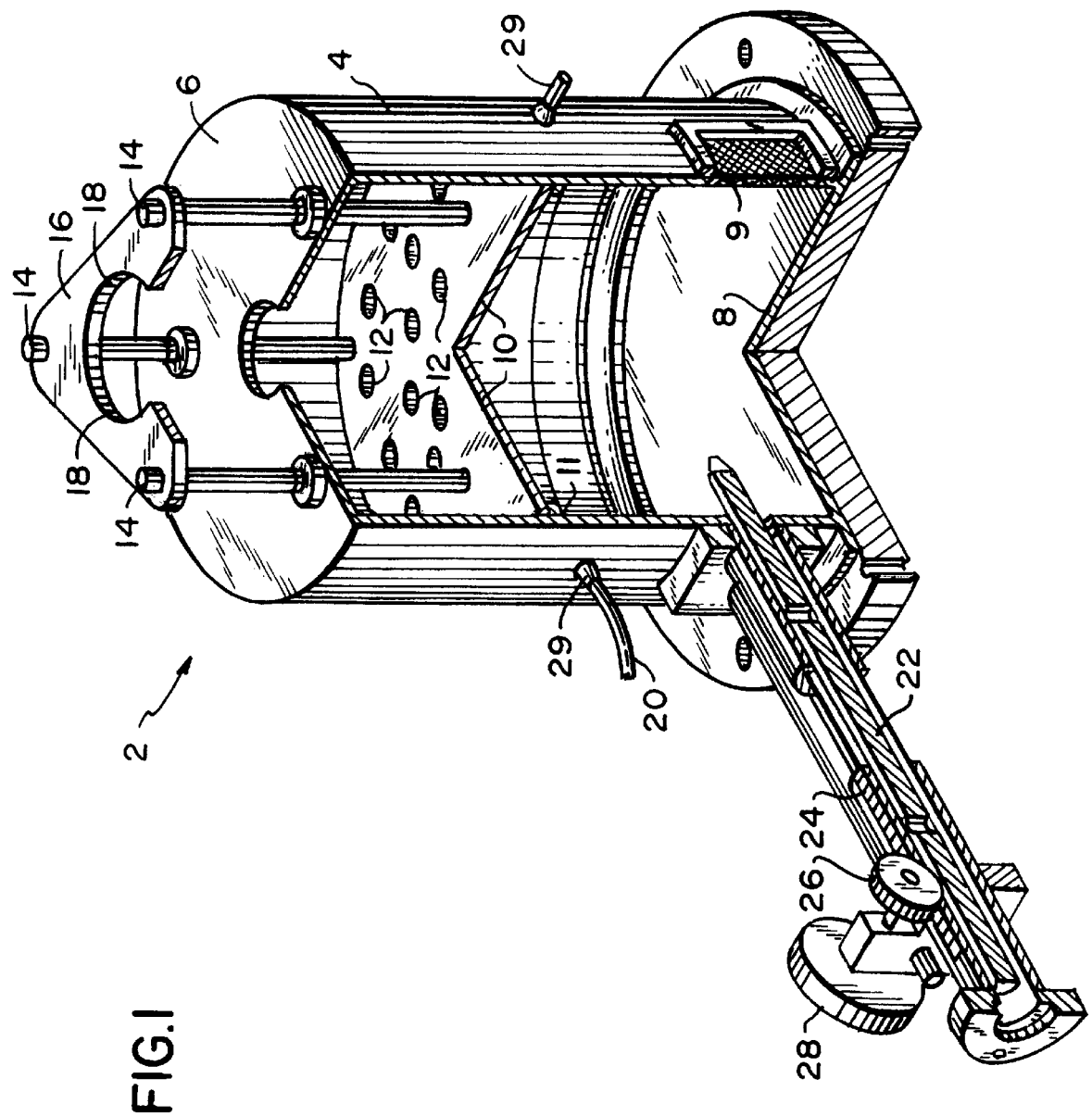
FIG. 1 comprises a three dimensional view of a tuneable microwave cavity processing system according to one embodiment of the invention.

In its broadest aspect, the present invention is a system for maintaining a cavity containing a work piece at resonance in which the physical parameters of the workpiece change on exposure to radiation.

In a more particular aspect, the present invention relates to a system for applying radiation to a workpiece in a cavity, The system has a means for producing a first signal indicative of the Q of the cavity; a means for producing a second signal indicative of the intensity of the radiation applied to the work piece; a means for producing a third signal indicative of the time rate of change of the temperature of the workpiece; and a means responsive to the first, second, third and fourth signals to produce a signal indicative of the value of the intensity of the radiation in the cavity and to maintain the cavity at resonance.

In another more particular aspect of the present invention, the first, second, third and fourth signals are signals in a computer which in response thereto produces a signal indicative of the value of the intensity of the radiation in the cavity and to maintain the cavite at resonance.

In another more particular aspect of this invention, the size and or shape of the cavity are varied based on the values of the inputs to maintain optimum operation. This may include movement of an antenna, coupling loop, short circuit or by moving the walls of the cavity, thereby varying the effective diameter for a cylindrical cavity.

It is another aspect of this invention to use a fifth signal input which measures the impedance of the cavity and provides a means to adjust the volume, shape of combination thereof or vary an impedance matching device to provide optimal transmission of the microwave energy into the workpiece.

These and other objects, features and advantages will be more apparent from the following detailed description, claims and the drawings appended thereto.

The present invention comprises the application of microwave radiation to physical processes and chemical reactions in a controlled manner so as to obtain products from these processes that are substantially defect free in a minimum amount of time.

The microwave radiation frequency is selected so that it will be absorbed by the sample and the electric field strength E is also selected between minimum (E min) and maximum (E max) values which are empirically measured so that the product obtained when irradiated at an electric field strength E will possess optimum properties. This method is applicable to physical processes such as drying samples e.g. removing solvent from polyimide precursors or water from ceramic materials and/or chemical processes such as the imidization of polyimide precursors and the curing of ceramic materials.

The present invention also comprises applying microwave radiation to such physical processes and chemical reactions in a tuneable microwave cavity so that microwave power is varied over time, based on the quality of cure factor "Z" (defined hereafter) in such a way to obtain a substantially defect free product in a minimum amount of time. The Z factor or cure fraction refers to the quality of cure or completion of the reaction whether a physical process or a chemical reaction in which the invention is employed.

Microwave radiation is applied to either a physical process or chemical reaction in order to obtain a predetermined value for Z or quality of cure factor which, in a tuneable microwave cavity, is a function of the Q factor (referred to as the quality factor), and temperature of the system. The Q factor in turn is based on the absorption of the microwave radiation applied to the process and in turn is measured by a comparison of the applied microwave power and reflected microwave power in the system over a range of frequencies or cavity heights and can be related to the dielectric loss factor for the workpiece in the cavity. Typically, the Q factor is calculated from a frequency sweep of the resonant cavity by rationing the resonant frequency with the width of the resonance at half height. An alternate method is to use a constant frequency and vary the volume of the cavity by moving a wall of the cavity or a cavity wall, thereby varying the diameter of the cavity. The value to which we will refer to as the Q factor is determined using the latter approach and in the simplest form, using the width of the tuning dip from resonance to a point with a preselected amount of reflected microwave power, e.g. 30% of the forward power. Where reflected microwave power is minimized (which is to say that a maximum amount of microwave power is transmitted into the cavity to be absorbed by the sample being dried or cured and a minimum amount of microwave power is reflected by the system) the system is said to be critically couple, or at resonance, which is the desired state. Since the Q factor varies with temperature and the change of physical state of the system (i.e. the change of the dielectric constant due to chemical and/or physical changes) the Q factor alone will not by itself provide a sufficient basis for obtaining maximum results from the application of microwave radiation to either the chemical reaction or physical process. Accordingly, the Z of the system which is a function of the quality factor Q and the temperature of the system is employed according to the present invention so as to provide an indication of how microwave power is to be varied over time (based on Z) in such a way as to produce a product that has been processed to a precise predetermined degree in a minimum amount of time. Microwave power is therefore varied over time based on Z in such a way to produce a substantially defect free material in a minimum amount of time where this power is applied either in a physical process (e.g. drying or solvent removal) or a chemical process (e.g. polymerization or curing a ceramic material).

The Q factor is determined for the system (which is based on the microwave apparatus, e.g. the cavity, the substrate on which the precursor is mounted, and the precursor and/or polyimide depending on the degree of imidization) combined with sample temperature and indicates when the precursor is substantially completely imidized or any degree of partial imidization is reached. The process therefore may be controlled to a reasonably precise predetermined end point and measured without removing the polyimide from the microwave apparatus or employing destructive testing methods for measuring the degree of imdization to the polyimide.

By employ ing the method of the invention a thirty fold reduction of the processing time has been obtained.

The invention may be employed in processes for coating integrated circuits such as microcircuits with polyimide films or any other substrate such as a semiconductor substrate, an electrical insulator substrate or any combination thereof, including metal and/or electrical wiring within the insulator substrate.

Utilization of a microwave apparatus that comprises a tuneable microwave resonant cavity that is tuned during the processing to achieve resonance of the system is essential to the practice of one embodiment of the invention.

The present invention in one embodiment comprises a system and apparatus for automated manufacturing of a material. The precursor is the work piece in combination with the microwave apparatus comprises a working apparatus. The workpiece is then irradiated with the microwave radiation. When the work piece is polyarnic acid it is irradiated to convert it to the polyibude or if the workpiece is a sheet-like material such as prepreg, solvent is removed from the workpiece or the resin on the workpiece is heated and reacted to some degree. The radiation may also be employed to initially remove solvent from the precursor in such a way as to avoid imperfections in the precursor such as voids, surface irregularities (e.g. pits) and the like One feature of the microwave apparatus is that it comprises a tuneable microwave resonant cavity means; another feature of the apparatus is it employs a variable power input whereby the power of the microwave radiation during the imidization is adjusted to control the degree and rate of imidization of the precursor.

It has also been discovered according to the present invention that the Q factor of the working apparatus changes as the workpiece physical characteristics change as a result of the irradiation and can be monitored during imidization. The process cycle can be stopped at any one of several Q factor temperature combinations, depending on the degree of change (imidization) that is to be achieved which in the case of a polyamic acid work piece is from freshly cast precursor in solvent up to substantially complete cure.

Figure 4:
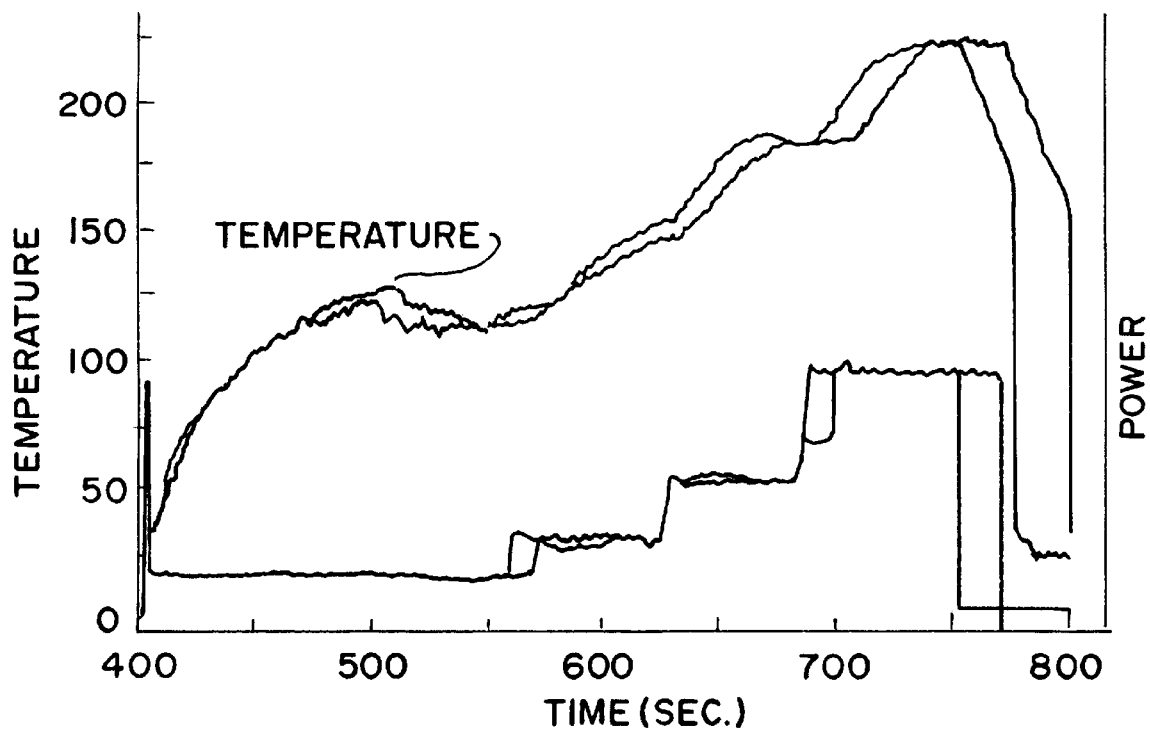
FIG. 4 is a plot of microwave power (Y axis) against time (X axis) applied to the microwave cavity of FIG. 1 and the resultant temperature of the precursor and/or polymer obtained over the period of time such power is applied for two successive runs.

The Q factor, as that expression is used throughout this specification, is the quality factor of the microwave cavity with the work piece therein (referred to herein as the working cavity) and is determined from the reciprocal of the width at half height of the resonant dip obtained as shown in FIG. 4 by monitoring the microwave power reflected from the power coupling to the cavity as the cavity height is varied. This is also illustrated in FIG. 4 where reflected power is plotted against height of the cavity.

In FIG. 4, reflected power is plotted along the Y axis and cavity height along the X axis for a single precursor containing polyaic acid (or ester) that is exposed to microwave radiation in such apparatus. Since the precursor absorbs energy relatively strongly in the initial pleases of the process, the width of the resonance curve (FIG. 4) will be relatively large giving a lower Q factor. As the imidization proceeds and solvent removed, less microwave power is absorbed by the sample resulting in a reduction in the width of the resonant dip in FIG. 4, thereby corresponding to an increase in Q. Since the absorption of microwave energy is temperature dependent, as governed by (the loss factor) and also the physical state of the film (e.g. glass or rubber) the Q factor will also be temperature dependent.

In each one of the time intervals, T1, T2 and T3 in FIG. 4 the microwave resonance of the tuneable cavity of the apparatus changes because the structure of the polyamic acid changes i.e. the polyamic acid/solvent combination is converted to a combination having mostly polyamic acid, some polyimide formation and some residual solvent to a material which is substantially solvent free and substantially completely polymerized to a polyimide with various degrees of imidization and solvent removal between the two extremes. This causes changes in the resonance of the cavity which is compensated for by tuning the cavity to maximum resonance (critical couplin) which corresponds to minimum reflected power (or zero reflected power). The tuning of the cavity is effected by moving the short 10 of the microwave apparatus upwardly or downwardly during the process and the coupling probe 22 in and out of the cavity.

As an example, power levels P1–P4 are applied to a polyamic acid precursor dissolved in solvent which is coated on a plate that is positioned on bottom wall 8 in the tuneable cavity 2 or FIG. 1. Power is applied for a period of four time intervals to develop Q values of 8,000, 9,500, 10,000 and 10,500 to initially drive solvent off from the film followed by partial imidization going up through substantially complete imidization. These steps may be summarized in the following Table 1.

| Power | Q | Temp | |
|---|---|---|---|
| P1 | 8,000 | 130–150 | Begin driving off solvent |
| P2 | 9,500 | 170 | More solvent driven off |
| P3 | 10,000 | 180 | Begin imidization, drive off residual solvent. |
| P4 | 10,500 | 250–350 | Complete imidization |

Figure 16:
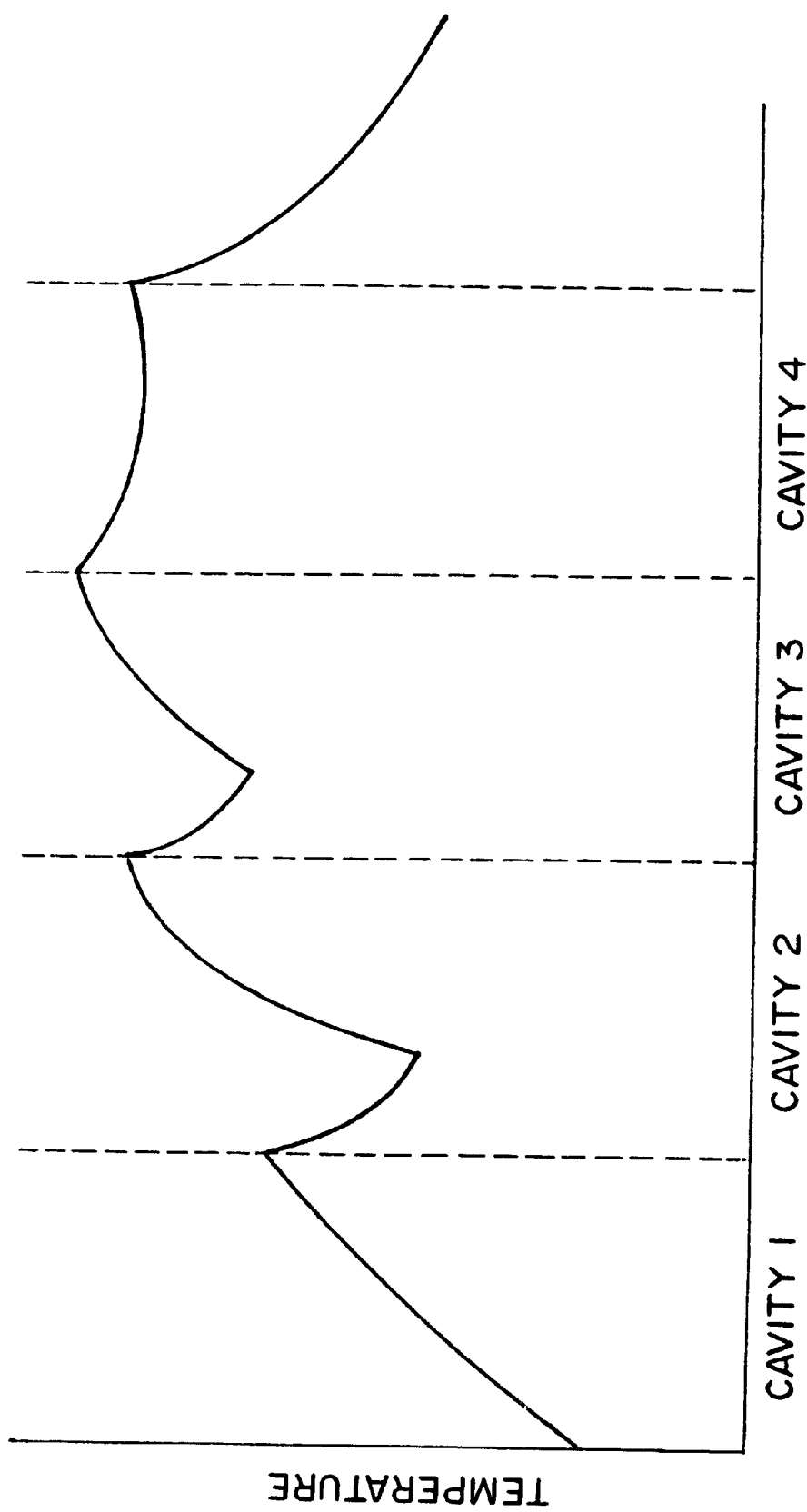
FIG. 16 shows a typical temperature-time profile as a web moves through a series of cavities in a continuous operation.

In the case where the workpiece is moving through the cavity in a continuous manner (instead of being stationary in the cavity as described above), regions P1 through P4 would physically occur in each of four separate cavities linked in series rather than in the same physical device but at varying times. Each cavity in such case has a dedicated microwave supply and temperature measuring device. This is shown in FIG. 16, where there are four zones or cavities in series and the workpiece moves through each of these in succession. There may be cooling between each zone depending on the speed of the workpiece (and in fact the slower the workpiece moves, the greater the cooling between zones). Each power level in Table 1 corresponds to a zone in FIG. 16 and each power level is controlled by the temperature of the workpiece within each zone independently.

The Q-factor coupled with the sample temperature provides a "quality of cure" factor "Z" which is a single value that describes the state of cure of the system (as determined by IR and the like). The analytical relationship between Z, Q and temperature can be determined from a series of measurements of Q, temperature and the degree of conversion of the precursor to the polyimide as determined by FTIR and equivalents thereof The Z factor therefore is obtained by measuring values of Q at a definite temperature and a definite degree of conversion and is an absolute value that can be measured for any reactants employing any microwave device and any workpiece whose physical characteristics change on exposure to radiation.

The Z factors can then be utilized to specifically indicate the degree of imidization to a polyimide of any subsequent run whether to obtain partial imidization or substantially complete imidization and thereby provides a method for the measurement of the degree of imidization without removing the material from the microwave apparatus. This is a non-destructive testing method for determining in situ the degree of imidization, but is not limited to imidization reactions.

Thus the invention is applicable to any process that absorbs microwave energy. The power of the microwave device is varied over time based on Z in such a way to produce a substantially precise end point of the reaction in a minimum amount of time to obtain a product of the desired quality, e.g. one free of voids and having substantially uniform physical and electrical properties. When microwave energy is applied according to the present invention for the manufacture of polymeric film s which can be foamed either because of the entrapment of products of reaction (alcohols and/or water in the case of the conversion or polyamic acid or ester precursors to polyimides) or because the precursor is employed in combination with a solvent, the microwave power is varied over time based on Z in such away to produce a substantially defect free film in minimum time.

Although the method of the invention has been described with reference to the manufacture of polyimide Films it is also applicable to the manufacture of any compounds and the sample or reaction milieu will absorb microwave energy whether for the manufacture of organic or inorganic compounds. For example, the process of the invention may be employed for the manufacture of laminates based on polyesters, epoxies, phenolics, acrylates and the like or the manufacture of such polyreric materials in non-laminate structures. Similarly, ceramic materials may also be dried and/or reacted employing the method of the invention.

The process of the invention can also be employed for removing solvents from substrates not only where the solvent in the precursor is removed by a controlled application of microwave power prior to curing but also for drying other materials such as removing the solvent from a photoresist to a precise level, removing solvent or the liquid reaction medium from the by-products of physical processes or chemical reactions especially those in which solvent removal promotes the growth of crystalline materials and the like.

Although the invention has been described with reference to a tuneable microwave cavity whereby the resonance of the system can be maintained by varying the cavity height or the radiation frequency or the position of the probe 22 in the cavity to match the impedance of the cavity, other systems which do not employ a microwave resonant cavity can also be employed and the process of the invention utilized.

Maximum properties with this type of apparatus can be obtained by varying the frequency of the microwave radiation, a sweep oscillator system being utilized in this latter respect. For example, a sample not in a cavity is exposed to microwave radiation by one or more microwave antennas similar to radar antennas.

The physical parameters which control the application of microwave energy to obtain maximum results such as imidization of polyamic acid precursors or physical processes involving the removal of solvents or liquids from samples, is both the radiation frequency, (i.e. the radiation must be absorbed by the sample) and the electric field strength. The power of the radiation is related to the square of the electric field strength. A sample, such as a polyimide precursor may be disposed on a surface to form a surface layer of thickness "d." Radiation is applied which is absorbed by the sample e.g. the precursor molecules generating heat at the sites on the molecules where the radiation is absorbed. This heat flows from the points of generation thereby heating the sample. Since a thin film has a large surface area (compared to its volume), much of this heat is lost at the surface preventing the sample from reaching a temperature sufficient to remove the liquid or solvent and to continue with the process such as imidizing the precursor. Therefore, the electric field must reach a minimum value, E min, before solvent or liquid removal and subsequent processing can occur such as imidization. At the same thickness "d," if the electric field exceeds a maximum value, E max, the sample temperature will rise too fast causing the solvent or liquid in the sample to boll generating bubbles which, in the case of imidizing a polyamic acid precursor, will get trapped as the viscosity increases and the solvent is driven off. The results in foaming of the sample. Therefore, for a sample thickness "d" where as max and E mn have a functional dependence on "d," as "d" increases, E max decreases because as the sample gets thicker the volatiles generated have a longer distance to travel or diffuse to the surface of the sample where the trapped gas is liberated. The E min curve increases as the sample thickness increases since the volume of the material increases with sample thickness. Power applied is proportional to $E^2$. At a given E, as the thickness increases, the power is absorbed by more material and therefore the temperature does not rise as much. Thus, as thickness increases E min must increase for the solvent to be driven off and for a subsequent imidization period. This is illustrated graphically in FIG. 5. By placing the system under vacuum, the absolute values of E min are reduced, and similarly the absolute values of E min increase if the system is placed under pressure, but the principal remains valid.

After the solvent is driven off, the process proceeds during which there is a minimum E to start imidization and a maximum E beyond which the rate of generating vaporized solvent during imidization will exceed the rate of solvent diffusion out of the sample resulting in defects in the sample such as the entrapment of vaporized solvent trapped as bubbles or foam or which may cause fractures in the sample.

In conducting the imidization according to the present invention and by employing the apparatus disclosed herein it has been observed that vapor produced during the course of imidization, if not removed from the system may condense on the surface of the polyamic acid and/or polyimide being formed causing irregularities in the surface which ultimately affect the physical properties of the polyamide. In addition, the film quality, void frequency, planarity and the like are affected by solvent condensation on the film during processing, The vapor in this regard comprises water vapor and/or solvent that may be employed to dissolve the polyimide precursor, the former being present primarily because of the dehydration mechanism by which the imidization of polyamic acid proceeds to the polyimide.

Accordingly, the microwave resonant cavity is provided with means for removing the vapor by using a perforated short 10 or screen in lieu of the perforated short to allow vapor to be removed from the chamber. Ports are strategically located around the periphery of the chamber communicating with the interior thereof which may be connected to vacuum means, pressurized gas or both. The gas may be an inert gas e.g. nitrogen so that an inert atmosphere may be provided around the sample.

It has also been discovered that improved film quality can be obtained if the process is conducted so as to remove the solvent prior to actively converting the precursor into the polyimide. This is obtained by adjusting the initial power of the microwave apparatus during the process so that the temperature of the precursor is sufficiently raised to drive off the solvent as vapor at a controlled rate prior to completion of the imidization so that the precursor and the polymer that is formed is substantially free of voids and solvent. The power of the apparatus is also adjusted to substantially prevent foaming and bubbling of the film while the vapor is being driven off so that the precursor and the polymer that is formed are non-foamed products i.e. the product obtained is substantially free of voids and solvent. Typically, precursors can be dried in two minutes as opposed to the prior art method employing a convection oven where the sample is treated at 130° C. for one hour in order to remove solvent.

The process of the invention is ideally suited for the application of a polyimide coating to any substrate and is especially adapted for coating or applying a film layer to a microcircuit or in the manufacture of sandwiched microcircuit structures. Polyimides may therefore be applied to semiconductor materials or electrical insulators and combinations of these with electrical conductors using the process and apparatus of the present invention, such process being especially adapted for the coating of alumina ceramics, glass ceramics, silica magnesium alumina, silica magnesium alumina with internal metal wiring, alumina with metal wiring and pads as well as metal lines, pads, etc. over Kapton (trademark) polyimides.

It has also been discovered according to the present invention that the process and apparatus as disclosed and described herein can be effectively used for preparing acetylene terminated polyimides in a fraction of the processing time ordinarily employed.

The key to processing the precursors for acetylene or other functionally terminated polyimides or polymers such as Thermid (trademark) 615, 601, PMR-15 (trademark) and the like (described by Bilow et al. U.S. Pat. Nos. 3,845,018; 3,864,309 and 3,879,349) lies in the ability to attain differential reactivities between the isoimide and the acetylene end groups, or the amic acid and acetylene end groups. Normally, this is accomplished by the very slow heating of the precursors. Fast heating results in the simultaneous reaction of both groups, leaving highly stressed polymeric films which have poor mechanical properties.

By employing the method and apparatus of the present invention the imidization proceeds in a controlled manner i.e., the amic acid or isoimide groups on the amic acid present in Thermid (trademark) 615 film have been almost totally converted to the imide form in three-five minutes without the reaction of the acetylene groups and almost complete solvent removal. The prior art methods of slowly heating these acetylene terminated polyamic acid materials resulted not only in the formation of polyimides but also the polymerization of the molecule through the acetylene groups as well. Thus, a new composition of matter is obtained in that the polyamic acid groups in this class of materials is substantially converted to a polyimide having acetylene end groups that are substantially unpolymerized and available for subsequent polymerization. This subsequent polymerization is obtained by post baking these materials in a conventional oven or microwave system, especially one having a tuneable microwave cavity or by using any other suitable heating means by which the imidization reaction is completed if not completed during the first microwave step and the acetylene end groups are reacted. Additionally, if not all of the solvent is removed in the first stage of the process it can be removed during post curing. The total processing time, (including exposing the precursor to microwave radiation according to the process of the present invention for from about three to about five minutes) is twenty minutes compared to eight hours using the prior art method.

The retention of mechanical properties of these acetylene terminated polyimides that are subsequently cured according to the process of the present invention can be observed from the DMTA chromatograms and stress-strain analysis, in which such materials are compared with a sample that is cured by conventional thermal means. The glass transition temperature is the same (within experimental error), the initial modulus is the same and the modulus above the glass transition temperature is the same. Furthermore, it is observed that Tg increases upon prolonged exposure at 400° C. and is exactly the same at 4° C./hour for both microwave treated and conventionally treated materials, indicating that the accelerated curing cycle of the present invention for this class of acetylene terminated polyimides is not detrimental to the mechanical properties of this material, contrary to when a very fast, high temperature thermal cure is used. Furthermore, the elongation at failure is the same, indicative of similar toughness between the microwave sample of the present and the slow thermal sample of the prior art.

Referring to the drawings, FIG. 1 illustrates a tuneable microwave resonant cavity apparatus 2 according to the present invention comprising cylindrical sidewall 4 with a topwall enclosure 6 and a bottom enclosure 8 having an inner surface on which a sample of polyamic acid precursor may be positioned. The apparatus 2 is also vented by means of opening 9 and nipples 29 in sidewall 4 or optionally elsewhere in the structure, eg. through the baseplate 8. A plate 10 is arranged to slidably engage the inner surface of sidewall 4 and has a sliding seal 11 positioned at the periphery thereof. Sidewall 4 may be constructed of stainless steel, the inner surface of which is highly polished so that it will more effectively reflect microwave radiation. The inner surface of said sidewall 4 may also be coated with a material that is highly reflective to microwave radiation but is also resistant to oxidation such as gold, siver-gold alloys and the like. The plate 10 is referred to as a "short" and has apertures 12 arranged throughout it so that any vapor in the chambers defined above and below short 10, sidewall 4, topwall 6 and bottom wall 8 can pass through such apertures. A screen, which will also function as a short, may be used in lieu of plate 10. A conduit 20 is connected by means of nipples 29 through sidewall 4 and opens into the chamber formed between sidewall 4, short 10 and bottom plate 8. Control rods 14 are securely attached to short 10 and held in a fixed spaced relationship relative to one another by means of plate 16 having opening 18 therein, control rods 14 being slidably moveable through topwall 6 by apertures therein arranged to slidably receive control rods 14. A microwave probe 22 is slidably mounted in the base of sidewall 4 so that it may be moved in or out of the chamber defined between the bottom face of short. 10 and the bottom wall 8 and sidewall 4 by means of rack 24 and pinion 26 or a threaded screw assembly operatively associated with a prime mover 28 which may be operated manually or by an electric motor controlled by a computer or manual controls. The microwave probe 22 is operatively connected at its exterior end (i.e. that end which does not project into the apparatus 2) to a microwave supply as will be further understood by reference to FIG. 2, the latter illustrating a microwave processing system 30.

The microwave power can be anywhere from 5 to 1,000 watts and especially 50 to 600 watts. A 500 watt power supply is a tpically used in one embodiment of the invention. Any frequency from 300 MHz to 120 GHz can be used as the microwave frequency of the microwave apparatus; specific useable frequencies are 915 MHz, 2450 MHz and 28 GHz.

Figure 2:
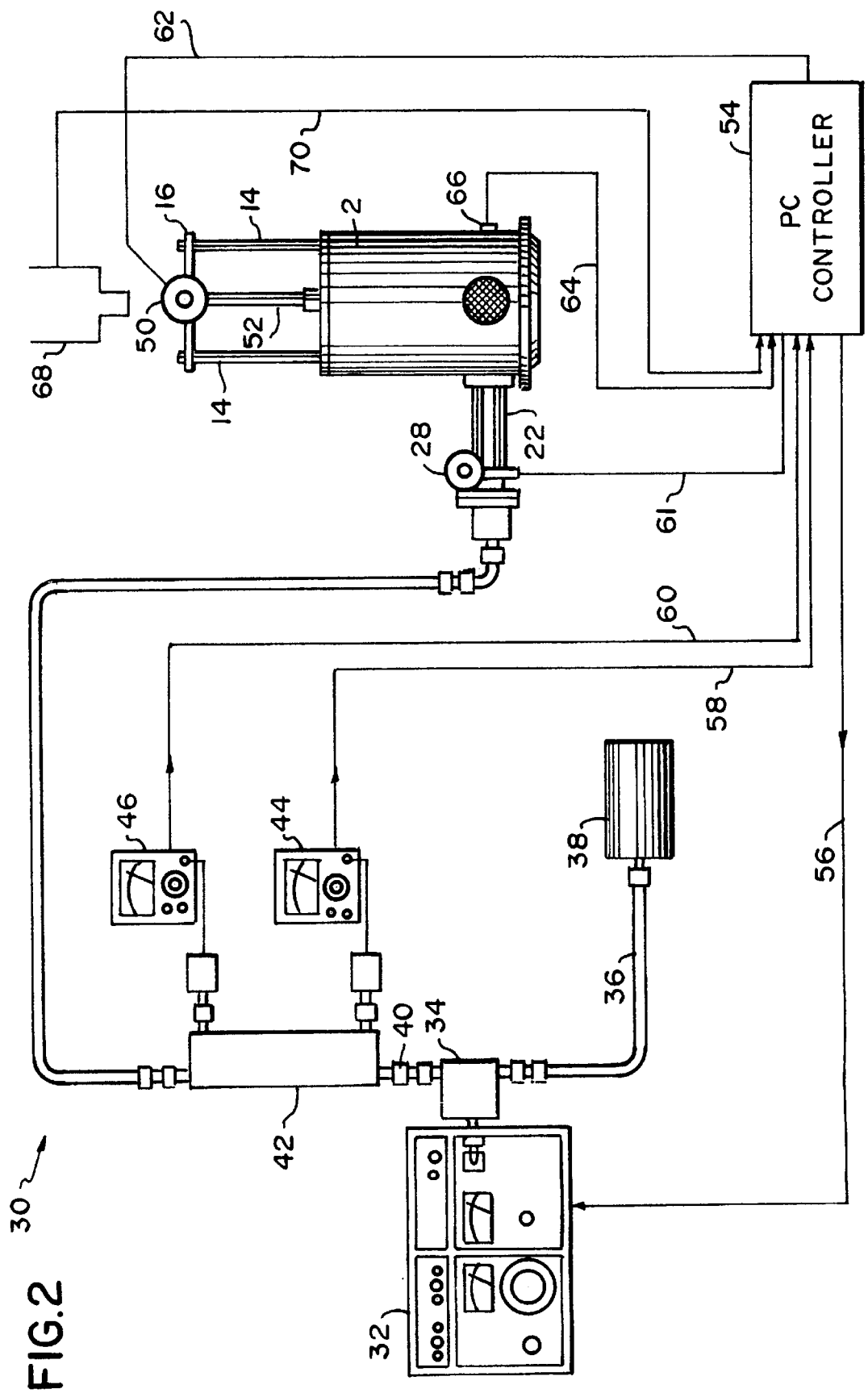
FIG. 2 comprises a flow diagram illustrating the connection to the tuneable microwave cavity of a microwave supply, three port circulator, directional coupler, power meters, dummy load, pyrometer and computer con troller for monitoring power output, temperature of the workpiece and the Q factor of the microwave cavity.

The microwave processing system 30 of FIG. 2 illustrates a microwave supply 32 such as Micro-Now (trademark) model 420B1 operatively associated with a three port circulator 34 such as Ferrite control No. 2620. The three port circulator 34 has a dummy load 38 such as NARDA 368BN operatively associated therewith by connector 36. The three port circulator 34 is also operatively connected to directional coupler 42 such as NARDA 3043B which in turn is operatively associated with power meters and sensors 44 and 46 such as a Hewlett Packard HP 435 device. Directional coupler 42 in turn is operatively associated with the microwave probe 22 by means of coaxial cable or suitable waveguide 48. The short 10 as described in FIG. 1 is moved upwardly and downwardly within the device 2 by means of prime mover (e.g. electric motor) 50 operatively associated with a worm drive 52 in a manner known in the art. A controller 54 comprising a programmed computer is operatively associated with microwave supply 32 by means of conduit 56, power meters and sensors 44 and 46 by conduit 58 and 60, prime mover 28 by conduit 61, prime mover 50 by means of conduit 62 and thermocouple 66 and optical pyrometer 68 by means of conduits 64 and 70 respectively.

In an example of an alternate microwave applicator, rather than varying the position of the short to vary the resonant frequency of the cavity, the diameter of a cylindrical cavity can also be varied to give a range of resonant frequencies.

The mechanics involved in moving two cylindrical halves 442, 448 of chamber 11 (FIG. 3) apart in a constant manner while maintaining parallelism is non-trivial. For the pair of cylindrical halves 442, 448 preferably approximately 4 inches in diameter, a movement apart of 0.1 inches results in a change in the resonant frequency of the applicator of 60 +/- 3 MHz. It is thus important to be able to move the cylinders apart over the diameter range of approximately 3.6 to 4.1 inches in a uniform and controlled manner.

Figure 3:
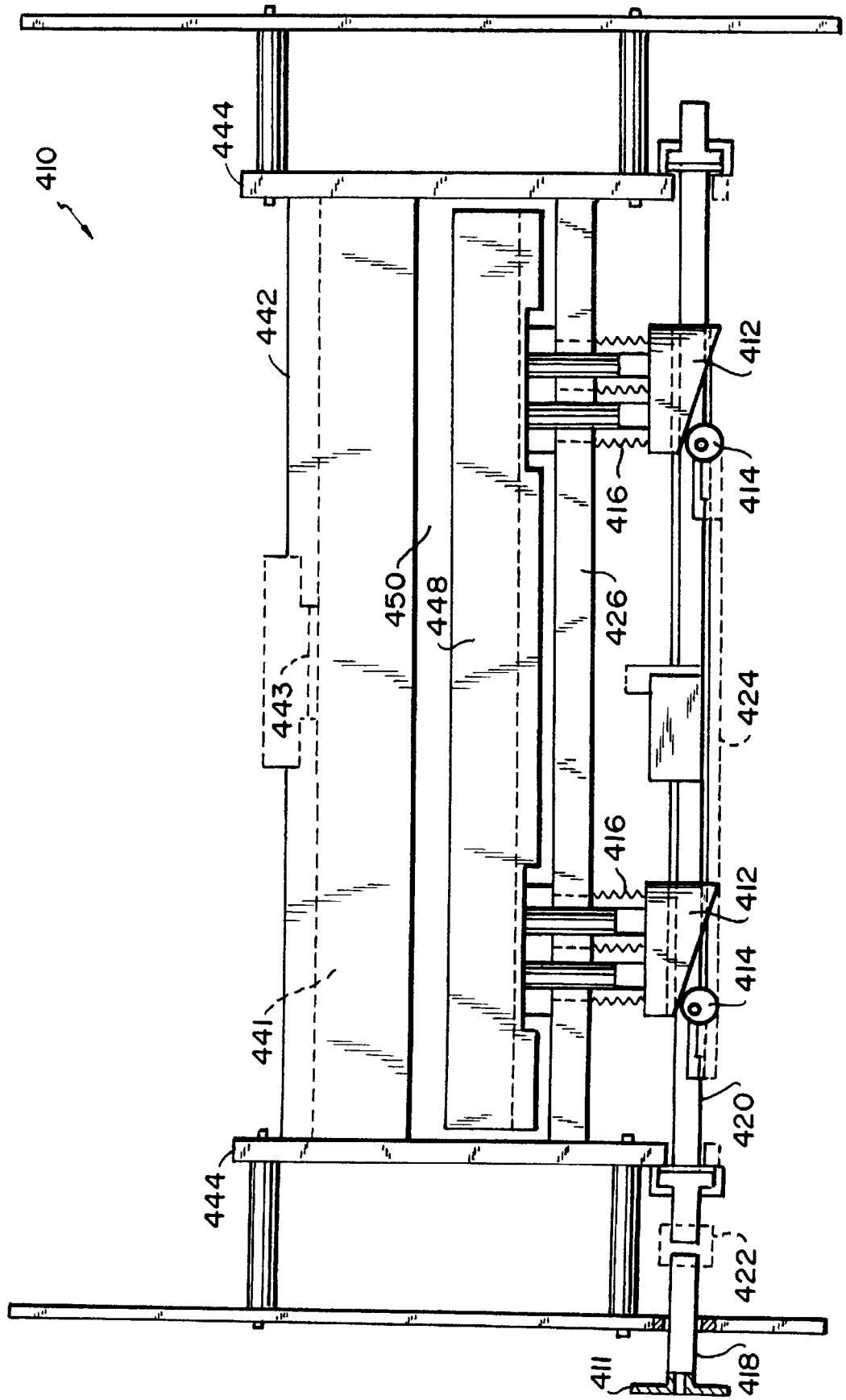
FIG. 3 is an example of how halves of a cylinder can be moved, thereby changing the volume of the cavity and therefore the resonant frequency.

FIG. 3 schematically illustrates one method of moving cylindrical halves 442, 448. A first cylinder half 442 is fixed between two support structures 444; and a second cylinder half 448 floats, e.g., is allowed to slide towards and away from first cylindrical half 442. The movement of second cylinder half 448 is governed by the movement of a threaded rod 420. A knob 410 is connected to a short shaft 418 which is coupled to threaded rod 420, by a collar 422. Threaded rod 420 is also fixedly attached to a plate 424, which has preferably four roller bearings 414 attached thereto. When threaded rod 420 is turned (by rotating knob 410), the rollers travel in one direction or the other. The rollers provide a camming action on inclined planes 412, which are attached to the floating second cylinder half 448, across a spring 416. Accordingly, second cylinder half 448 can be moved towards and away from first cylindrical half 442 by rotating knob 410 in the appropriate direction. The above operation may either be performed manually or in a fully automated fashion through computer control. The second cylinder half 448 is an electrical connection with the supports 44, via flexible conductive materials.

The design of applicator 410 is useful for processing web-like materials. Such materials may be inserted into applicator 410 through a space 450 provided between first and second cylindrical halves 442, 448 (i.e., the web moves orthogonally to the plane of the drawing). As such, the range of motion of second cylindrical half 48 may be limited to provide a desired spacing between first cylindrical half 442 and second cylindrical half 448 depending on the dimensions of the materials to be processed.

Similar principles exist regarding the operation of either a short in a cylindrical cavity or changing the diameter of a cylindrical cavity. Furthermore, ANY shape cavity can be operated in a similar manner (including spherical, rectangular, hexagonal, etc. Although a significant amount of the teaching is specifically referring to movement of a short, this is for brevity purposes and is purely one example of the mode of operation. For example, prime mover 50 is substantially the same as knob 410 (if a motor were substituted).

In use, and referring to FIGS. 1 and 2, a polyamic acid precursor is dissolved in a solvent and coated on a base such as a microcircuit and the microcircuit thus coated positioned within the cavity between bottom wall 8, sidewall 4 and short 10 of apparatus 2. The microwave supply 32 is turned on and microwave radiation is caused to radiate from probe 22 within the chamber of apparatus 2 probe 22 being moved in or out of the chamber to match the impedance of the system as the dielectric constant of the system changes. The power is controlled by the programmed controller 54 in response to the temperature of the sample in the chamber 2 as measured by pyrometer 68 and the temperature of the cavity as monitored by IR pyrometer 66 or an equivalent thereof. The reflected power from the apparatus 2 is measured by power meters and sensors 44 and 46 which in turn relay this information to the controller 54 which conveys a programmed response to the prime mover 50 so that the short 10 may be moved upwardly or downwardly and the probe 22 moved in and out of the microwave resonant cavity within the apparatus 2, so it may be tuned to achieve minimum reflected power and hence critical coupling for the system, as the system is defined herein. The controller 54 is programmed, in one instance to provide power to the apparatus in a manner to obtain the temperature over the time period as illustrated in FIG. 4. The application of power to attain the temperatures as set forth in FIG. 4 and movement of the short to attain the critical coupling may also be effected manually rather than by utilization of controller 54.

A feature of apparatus 2 comprises means for removing vapor from the chamber thereof so that such vapor (e.g.

solvent and/or water) will not condense and redeposit on the sample being processed. As illustrated in FIG. 1, apertures 12 are provided which allow vapor developed during processing of a sample in the chamber below short 10 (as that chamber is defined herein) to pass into the upper chamber and either condense in the upper chamber or to be vented through an opening in plate 6 or by means of conduit 20 which optionally is operatively associated with a vacuum pump to more completely evacuate the chamber below short 10. Opening 9 at the bottom of sidewall 4 or nipples 29 allows for an external fluid such as dry purified dust-free air or similar gas to enter the bottom of the apparatus 2 and be withdrawn through conduit 20. Optionally, short 10 can comprise a non-perforate plate (i.e. a plate without any openings therein) and the apparatus 2 can be evacuated by a series of conduits strategically placed along the length of sidewall 4 and operated simultaneously or serially to evacuate the chamber above or below short 10 as those chambers are being varied in volume depending on the movement of short 10 upwardly or downwardly along the inner surface of sidewall 4.

The opening 18 in the plate 16 is provided so that the pyrometer 68 may be focused on the sample through an opening in top wall 6 and short 10 that is aligned with opening 18 and through which the optical pyrometer 68 may be aimed. A fiber optic temperature probe may be used in lieu of the pyrometer and focused on the sample through an opening in the sidewall 4 rather than from above.

The invention also relates to systems which have been developed that allow the computer to maintain cavity resonance by monitoring the reflected microwave power and acting so as to minimize the reflected power by the adjustment of the sliding short 10 and the input probe 22.

Figure 5:
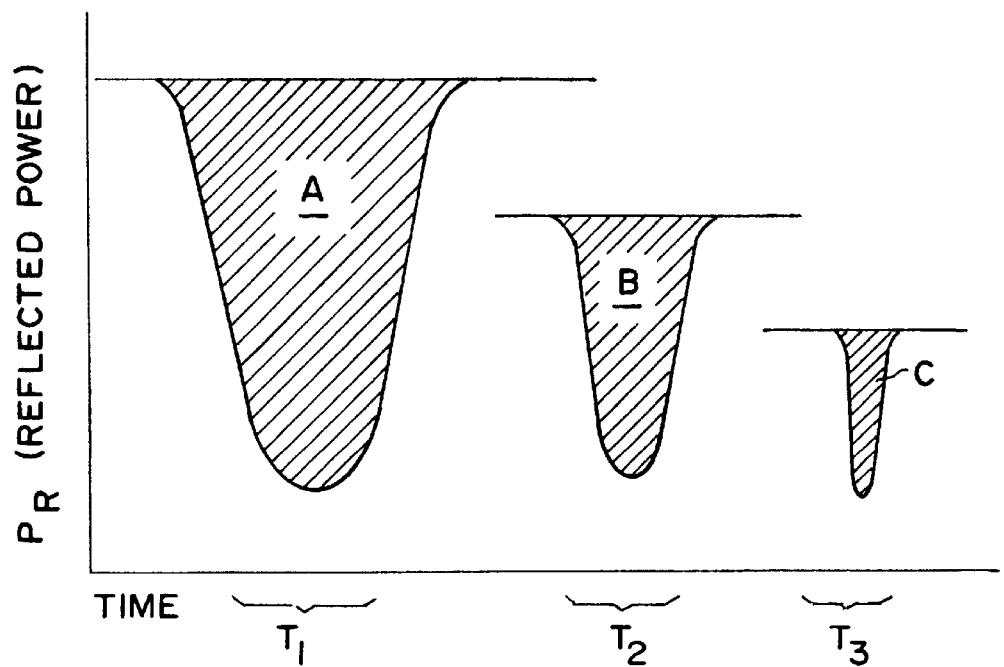
FIG. 5 comprises a plot of the reflected microwave power against the height of the cavity of the apparatus of FIG. 1, wherein the Q factor (i.e. quality factor) for the system is related to the reciprocal of the width at half height of the resonant dip (for constant frequency input) obtained by monitoring the microwave power reflected from the coupling to the cavity.

Initially, a system programmed into controller 54 causes the sliding short 10 to be returned to a "home" position below the desired resonance. Short 10 is then raised in a step wise manner followed by reading the reflected power after each step on meters 44 and 46. When the reflected power decreases below a threshold value, indicating an approach to a resonance dip as illustrated in FIG. 5, the step size is reduced and the direction of the step is now controlled depending on the sign of the difference between the last two data points and the absolute position of the short where those two power values were measured. As the reflected power continues to decrease below other thresholds, the step size is further reduced. If the reflected power reaches a local minimum, the computer program in controller 54 produces a signal which causes the movement of the input probe 22 so as to match the impedance of the cavity, using a similar difference between the reflected power and absolute position to determine in which direction to move to further reduce the reflected power.

This routine is capable or reducing the microwave power to less than 0.1 percent of the forward power reflected from the cavity. More importantly, the routine "tracks" a curing polymer system, resulting in the system maintaining resonance during the complete processing cycle.

A second system programmed into controller 54 requires the short 10 to move over a large distance, passing the resonance dip, while recording the level of the reflected power and then returning the short to the position where the minimum was found. If reflected power is not zero, a similar routine, generated by processor 54 operates on the input probe 22 to find a minimum for that axis and program execution returns to find the position of the reflected power minimum for the short period. This iteration continues until the reflected power is zero. Either this second routine or the above first routine can then be invoked to maintain resonance for the remainder of the processing cycle. Typically these routines take only about 15 seconds to find resonance.

A third system programmed into controller 54 requires the short to be returned to a home position at the beginning of a process cycle (or at power start-up). Thereafter, the short moves in a predetermined direction at a predetermined speed while monitoring the reflected power on meters 44 and 46 until the reflected decreases to a predetermined fraction of the forward power (usually about 70%). Thereafter, the direction and step size that the motor takes is dependent on the slope of the reflected power over time, d(reflected power)/dt, hereinafter referred to as "S" taken over a suitably few number of points to ensure that the response is not overdamped but that noise is largely eliminated. Provided S is less than 0, the direction is not changed, however, if S becomes greater than 0, the direction is changed and the antenna or second tuning device is moved using a similar algorithm. The step size is based on a predetermined multiple of the magnitude of S, the multiple being different for the antenna and short. If S is near zero (when approaching a true minimum), the reflected power as read from 44 and 46 is read and if the reflected power is close to zero—less than a predetermined value, usually about 5–10% of the forward power, the motors are stopped until the reflected power increases above the predetermined minimum and S becomes positive. Similarly, the diameter of the cavity can be varied rather than the short being moved.

Figure 7B:
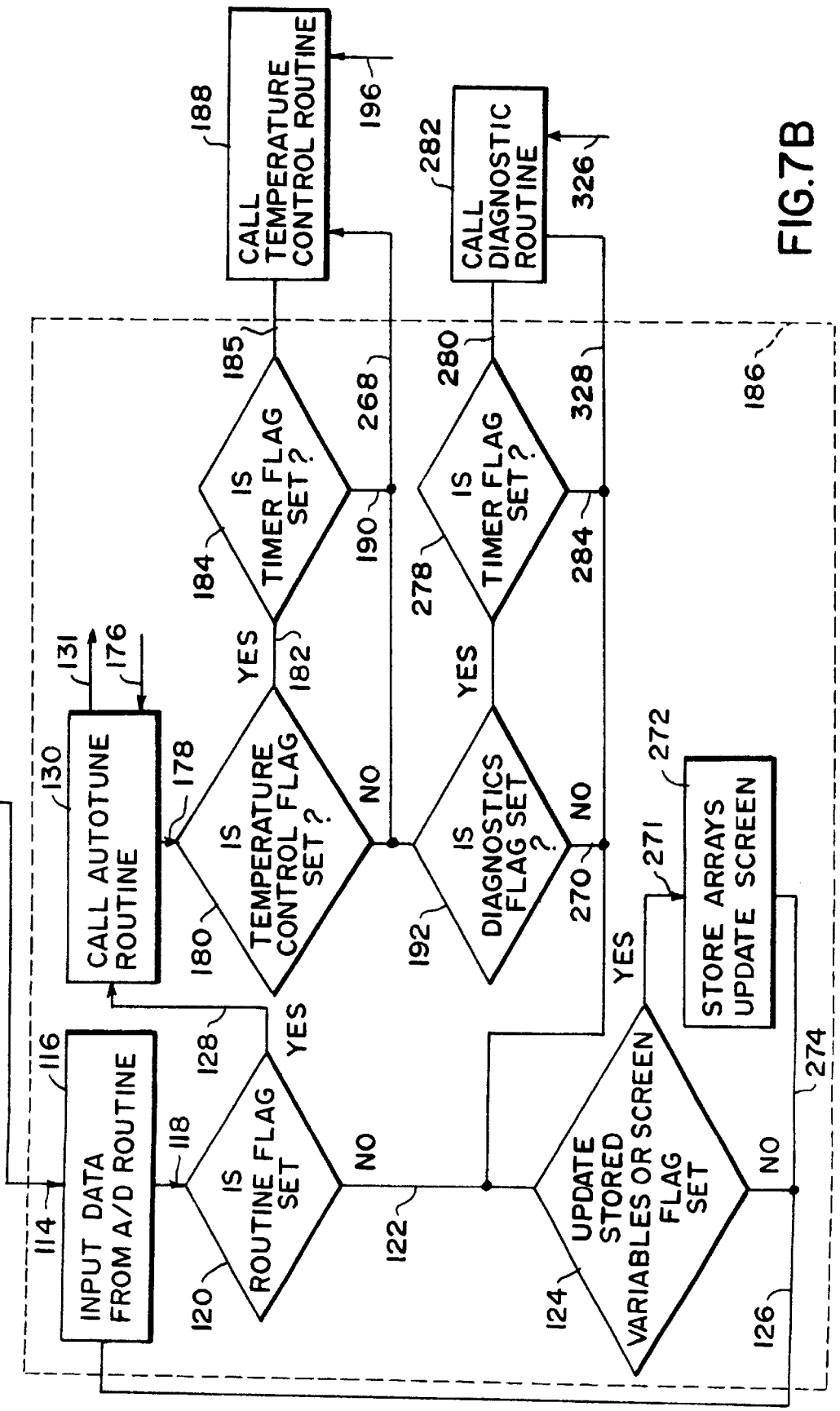

FIG. 7 shows a flow chart for the design of the overall control system according to the present invention.

The control system for the present invention can operate on any computer for example, an IBM 370 computer, an IBM Personal Computer, such as a PC/AT or a more sophisticated model, and any other stand alone computer having similar capability can be used. The program language used to program the control system according to the present invention can be any suitable language such as basic, fortran, assembly language, C language and the like.

Figure 15:
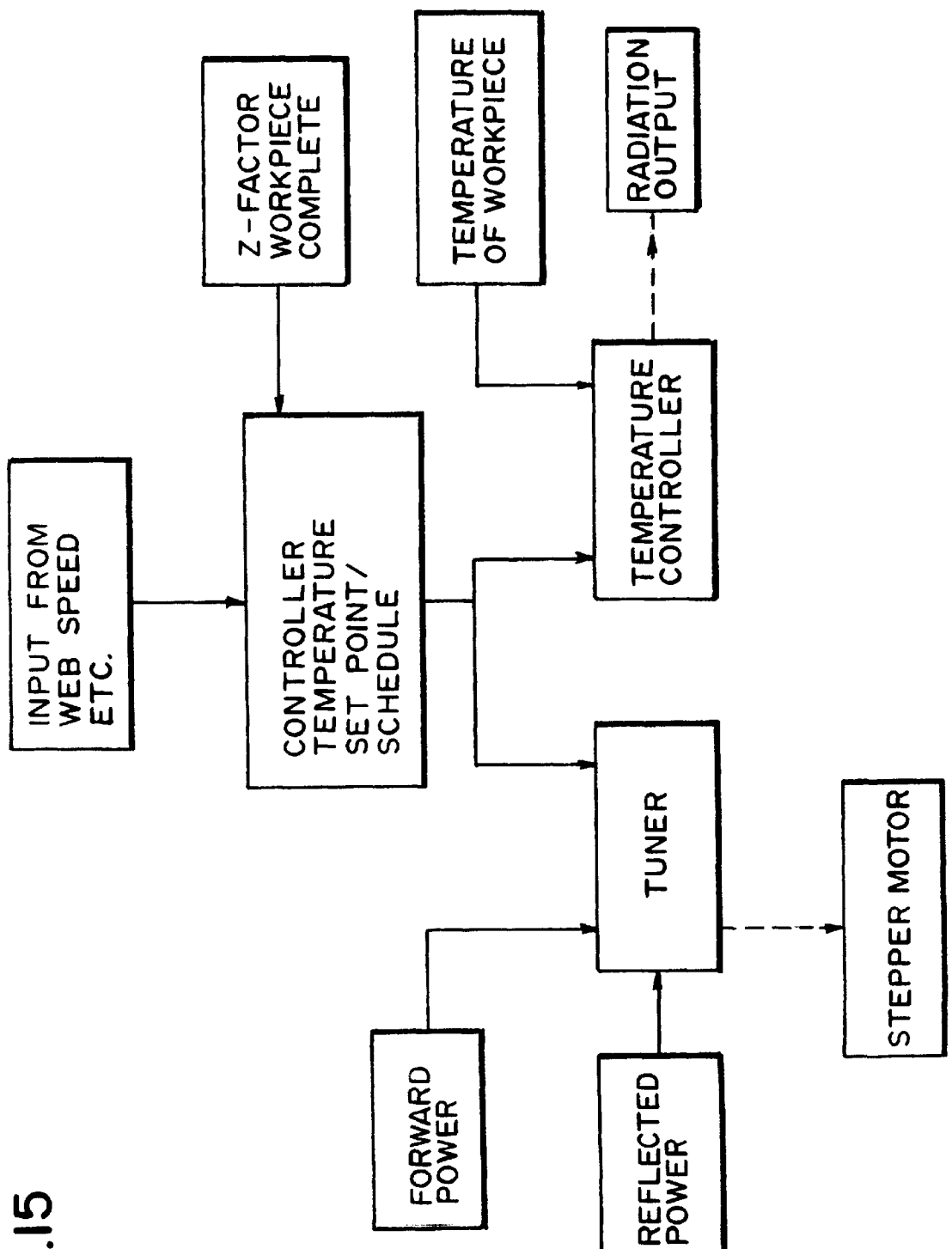
FIG. 15 shows a schematic of operating this invention where a number of discrete controllers are used to control one or more individual aspects of this invention each coordinated from a central controller

Additionally dedicated motion controllers can be used which have their own unique "language". Furthermore, discrete units can be used to control a particular aspect of the invention, with signals from these devices being received and sent from a central controller. FIG. 15 shows a schematic of a system which can perform this invention in which a discrete temperature controller and a discrete controller to tune the cavity are connected to a central control computer which issues signals to change temperature or indicate when to start tuning, etc. Essentially, the subroutines from an integrated computer system can be enabled by specialized hardware and the program does not have to reside within a single device and operate in the same fashion.

Block 100 of FIG. 7 represents the system call or the command to execute the control system. Line 102 represents a signal for passage of control to block 104. Block 104 represents the initialization of the A/D convertors for power meters 44 and 46. The A/D convertors arc 16 channel A/D convertors (model number DAS-16 manufactured by Metrabyte). The A/D convertors need at least three inputs, one for temperature, one for incident radiation power and one for reflected radiation power. Directional coupler 42 strips off 1% of the input power and 1% of the reflective power and directs into meters 46 and 44 respectively (these meters are Hewlett Packard Microwave Power Sensor meters Model Number HP 435 B). When the A/D convertor is first initialized the multiplexer is set up to read at a predetermined repetition rate specified in the program the incident and reflected power at preferably from 20 to about 30 times per second. Temperature is monitored by pyrometer 68 which is fed into the A/D convertor or alternatively communicates to the controller via a RS-232c interface or similar. The input to the AMD convertor from meter 44 is line 58, the input from meter 46 to the A/D convertor is line 60 and the input from pyrometer 68 to the A/D convertor is line 70 of FIG. 2. The output from meter 44, meter 46 and pyrometer 68 produces an input to the A/D convertor which generates a signal indicative of input power, reflected power and temperature in the computer on which the control system is running. Block 104 also corresponds to initializing the timer of the computer to correspond to the running time of the program. Every ⅛sth of a second corresponds to one count in the timer. Therefore, the counter which is initialized at the beginning of the call of the program to zero is incremented by one at every ⅛sth second time interval. Block 104 corresponds to setting up of the following interrupts which are used during the running of the control system. Set system timer interrupt to point to a subroutine which counts events. When sufficient counts have been received to allow an event (e.g. plot the data on the screen) a flag is set in the interrupt routine, which is then read and acted on accordingly by the program during normal operation. After execution of the interrupt subroutine, program execution resumes at the point at which the interrupt occurred.

The controller 54 of FIG. 2 interacts with prime mover 28 of probe 22 and prime mover 50 of short 10 by means of a standard serial interface digital communications port RS232C for output to stepper motors (model Number 57-51 fabricated by Compumotor) used for the prime movers 28 and 50.

Line 106 represents a signal passage of system control to block 108. Box 108 represents presentation of an options screen on a display means such as the CTR display of an IBM Personal Computer. Creation of option screens in C language is described in, for example, Borlond Turbo C Reference Guide (Borland International). Any reasonable number of options are presented at this level, of which seven are activated and can be selected by the operator of the control system. Option one controls the output to a display terminal which plots temperature versus time, fosard power versus time, and reflected poaer versus time. The scale of the vertical and horizontal axis are set in option one. Option two controls a plot of the Q of the cavit versus time. The horizontal and vertical axis of the Q versus time plot are controlled in option two. In option three the sensor from which the temperature versus time data for the plot of option one can be set. In the preferred embodiment, only one monitor of temperature for the work piece is utilized in the control routines described herein below. Option four specifies that only the data of temperature, forward power and reflected power are to be acquired versus time without a call of the temperature control routine or the diagnostic routine both of which will be described herein below with reference to FIGS. 9 and 10. In option 5 the automatic tuning routine only can be selected in order to minwmize reflected power without running the temperature control routine or the tune diagnostic routine as defined herein below. while simultaneously acquiring the data described in option 4. In option 6 the operator can select running of the temperature control routine and the automatic tuning routine without selecting of the diagnostic routine. In option 7 the operator can select the diagnostic routine, the temperature control routine and the auto tune routine, which is defined as the complete control system.

Figure 11:
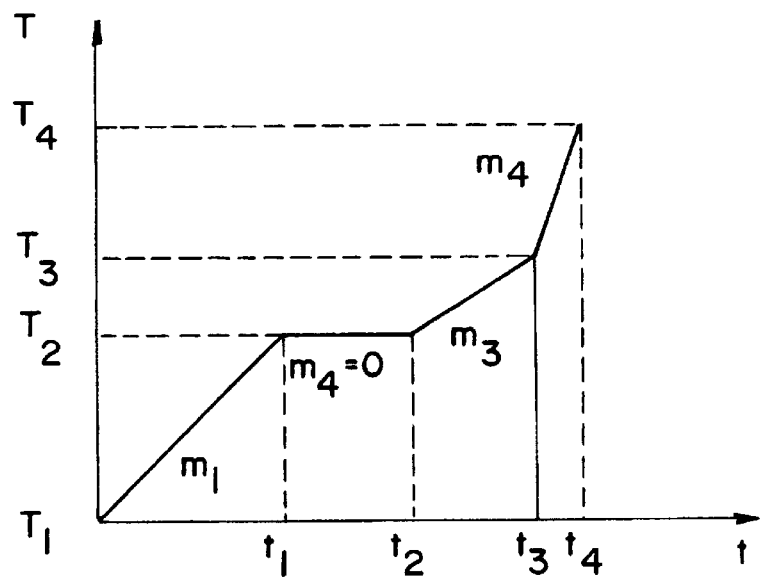
FIG. 11 is a typical temperature time profile showing the manner in which segments are used to input the desired profile to the program.

The temperature control subsystem as Aill be described in greater detail herein below, looks to a data set which contains data for the applied temperature versus time schedule. For example, FIG. 11 shows schematically a plot of a temperature versus time schedule. The data for this is placed in a data set which has groups of three numbers. The first number being a initial temperature for the first time interval, the second number being the linear time rate of change of the temperature and the third number is the time of duration of a constant temperature hold or soak. Referring to FIG. 11 the data read from a file corresponding to the versus time schedule of FIG. 11 would be: $T_1$, $m_1$, $t_2-t_1$; $T_2$, $m_3$, O; $T_3$, $M_4$, O. The times $t_2-t_1$ as necessary are determined by the current value of the counter described herein above, For the time interval between time $t_1$ and $t_2$ the time rate of change of temperature with respect to time $m_2$ equals 0 which means that the work piece is held a temperature T2 for a time $t_2-t_1$, which is commonly referred to as a soak or a hold at temperature $T_2$. The referred to change of temperature with respect to time can have values which are positive, negative and 0.

As represented by block 104 every ⅛sth of a second the program sets up a flag which increments the counter so th at the program can keep its own time. The measured data for temperature, forward power and reflected power is saved and the screen to which the plots can be made is updated once per second.

Therefore, once every second an additional data point is added to the plot which is on the screen to eventually completely fill out the plot. The determination of Q is done once every 5 to 30 seconds (the frequency at which Q is determined, that is once every X number of seconds is determined from option 2, box 108). The time is determined by the value n in the counter where the actual time is N×18. When N is 18 this corresponds to one second. The time interval at which Q is evaluated is set by typing a number onto the screen presented as a result of block 108. If no value for this time interval is entered, a default valve is loaded.

Line 110 represents a signal for transfer of program control from block 108 to block 112. Block 112 presents the screen on which the plots referred to herein above are presented. On the upper left hand corner of the screen is a list of the options including start run, save data, change microwave power, start/stop auto tune routine and change stepper motor increments (for manual) movement of stepper motors (28 & 50 in FIG. 2). At the upper righthand comer of the screen is presented the current value of the data which is being plotted on the screen that is the current temperature, forward power, reflected power and heating rate. At this screen there is a hold which is waiting to be released by the press of a key stroke to permit the program control run to start.

FIG. 4 is the type of plot which is plotted on the display screen when all of the data is acquired. The plots of FIG. 4 are built up over time with the data being updated once every second. At block 112 other options other than to start a run can be selected. These can be conveniently controlled by the F keys on the key board of an IBM Personal Computer. Other options besides program start can be to save the data into a data set or data location, turn off or on the autotuning routine no matter which options have been previously selected at block 108 and select the radiation power to be applied directly from the keyboard, Other options are within the scope of the art and can be added at this point of the control routine. How to control the F keys and display plots at the terminal can be found in any language manual, e.g. Turbo C Reference Guid Version 2.0 from Borland International. At block 112 motor 50 controlling short 10 is advanced to move the short as close to the work piece as possible. Motor 28 is advanced to withdraw antenna 22 as far out of the cavity as possible in order to find the zero of the location of the antenna and it is then advanced in towards the workpiece to an average position which has been previously determined by experimentation to be a preferable starting position to the location of antennae 22 for the minimum power reflection. The actual position of this antenna does not need to be known accurately since the control program automatically optimizes this position. The approximate value of the starting position can be found by operator intervention or using the position for the empty cavity.

Line 114 represents a signal for transfer of system control to block 116. Block 116 represents the system receiving data from the A/D convertors which receive input signals from forward and reflected power monitors 46 and 44 and from pyrometer 68. Data is continuously fed into the system controller as signals indicative of the applied power level, the reflected power level and the temperature of the sample as part of block 116. Line 118 represents a signal for transfer of program control to block of 120.

In block 120 there is a test made to determine if the autotune flag was set in order to call the autotune routine. The autotune routine flag is set in block 108 as previously described. If the autotune subsystem flag has not been set, system control is passed by a signal represented by line 122 to block 124 where a test is made to determine if the screen flag is set and whether the flag to update stored data variables is set by the interrupt subroutine. If the flag to update store variables or to update the screen is not set program control passes from block 124 by a signal which is represented by line 126 back to block 116.

Figure 8:
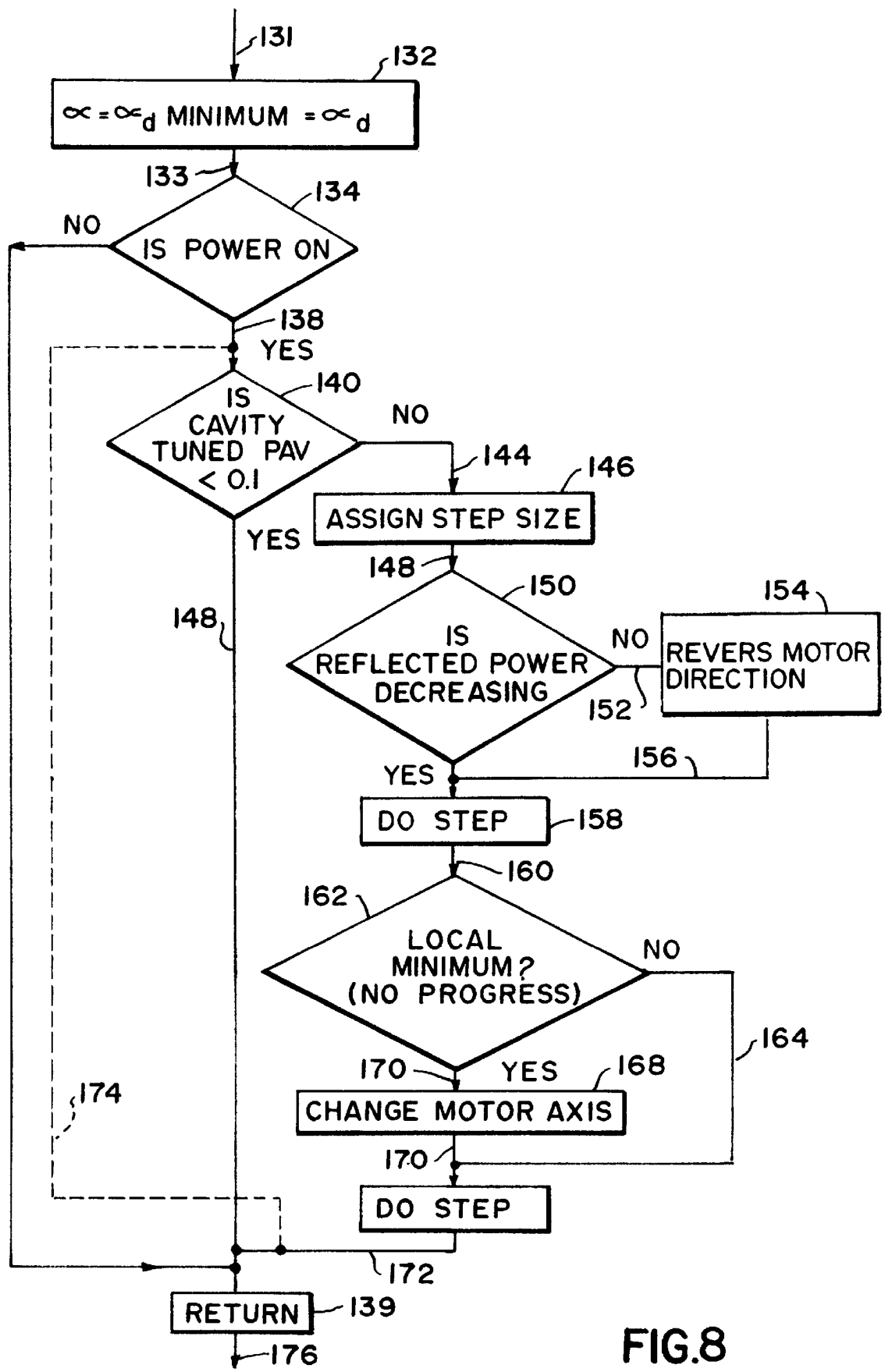
FIG. 8 is a flow chart of the control system of the invention.

Returning back to block 120 if the autotune flag is set. (Typically being set is to be set to one) program control passes from block 120 by a signal as represented by line 128 to block 130 which is a call to the autotune routine which is shown in FIG. 8. Transfer of program control to the autotune routine is by a signal represented by line 131.

Figure 6:
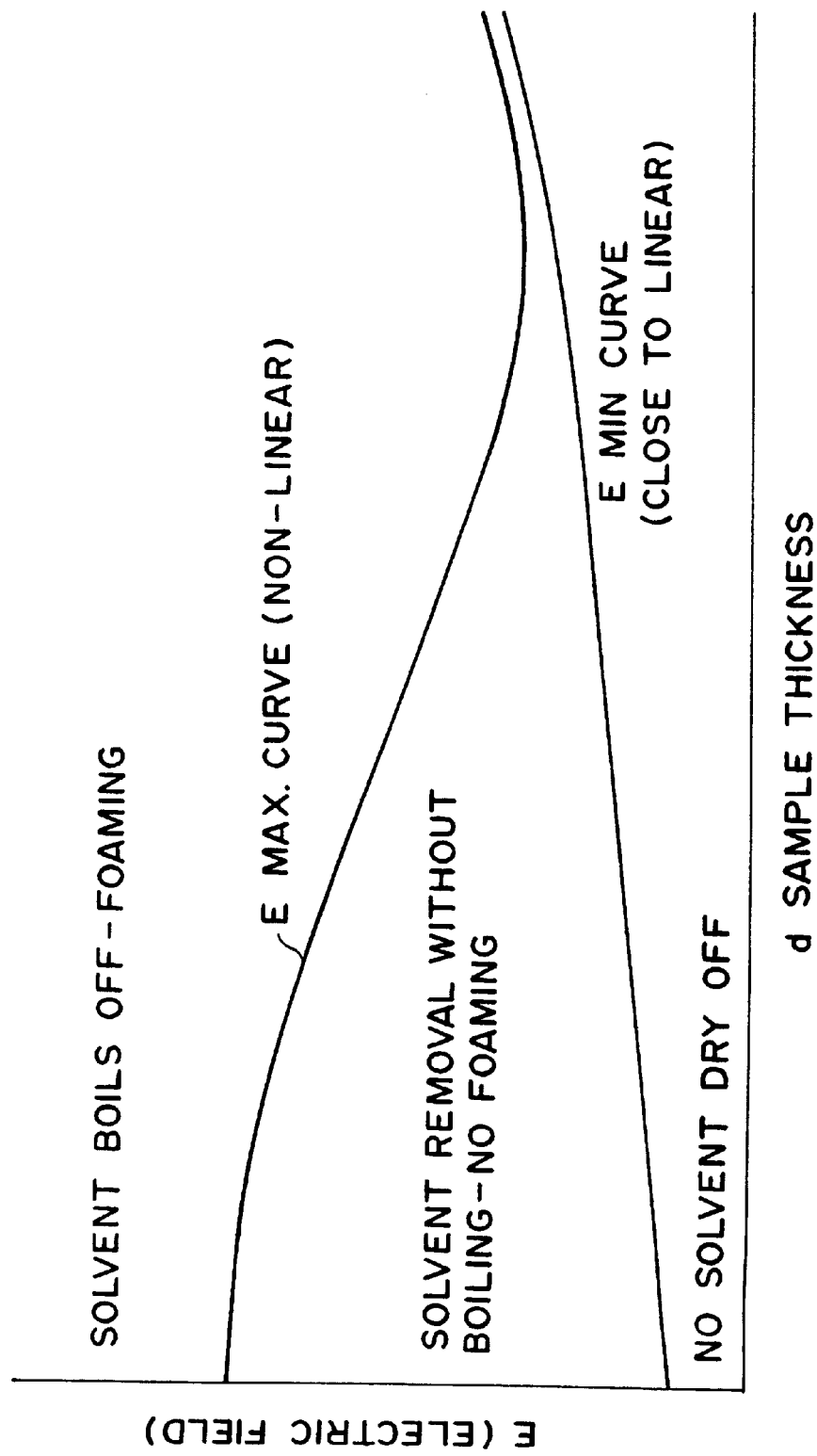
FIG. 6 comprises a plot of the electric field strength E of microwave radiation employed according to the present invention where the power of such radiation is directly related to the square of E. The electric field E is a value on the Y axis lying between E max and E min for a polyimide precursor dissolved in the solvent and is obtained by establishing where solvent removal is obtained without boiling i.e. no foaming, which is a value between E min, where electric field is too small to result in solvent drying and E max, those values where the solvent bolls off causing foaming of the polyamic acid at various thicknesses "d" plotted along the X axis.

Line 131 of FIG. 8 represents the call to the autotune subsystem which leads to block 132 α is set to the value of the ratio of the reflected power to the forward power. In block 132 the first of the group of the short and the antenna to be moved to tune to cavity is defaulted to the short. At block 134 a test is made to determine whether the radiation power is on. If the radiation power is not on program control is transferred by a signal as represented by line 136 to box 139 which is the return signal as represented by line 176 to block 130 which is the call to the autotune routine. If at block 134 as a result of the test it is determined that the microwave power is on, program control is transferred by line 138 to block 140. At block 140 a test is made to determine whether the cavity is tuned. The cavity is defined to be in tune if α is less than a predetermined value preferably 0.1%. If the cavity is found as a result of this test to be in tune, program control is transferred by a signal as represented by line 142 to block 139 which is the return to block 130 of FIG. 6 which was the call of the autotune routine. If the cavity is not in tune, system control is transferred by a signal as represented by line 144 to block 146.

In block 146 tile step size for the prime moves 28 and 50 of FIG. 2 are set according the following equations. The prime movers are motors Compumotor, Model 57-51 which make 12,800 steps per 360° of rotation. The total number of steps advanced based on tle test of α is called the increment. The test is as follows: if $0.1 \leq \alpha \leq 0.25$ then the increment is 50 steps; if $0.25 \leq \alpha \leq 0.4$ than the increment is 80 steps; if $0.4 \leq \alpha \leq 0.65$ than the increment is 130 steps; if $0.65 \leq \alpha \leq 0.8$ than the increment is 180 steps; and, if $0.8 \leq \alpha \leq 1$ than the increment is 250 steps. Optionally, the increment can be set equal to the ratio of reflected power to the forward power (α) times a constant plus an offset wherein the constant and the offset are inputs which can be input at the option screen represented by block 108 of FIG. 6.

System control is passed from block 146 by a signal as represented by line 148 to block 150. In block 150 a test is made to determine whether or not the reflected power is decreasing or is not decreasing. If the reflected power is not decreasing, that is the current value of reflected power is greater than the previous value of reflected power, program control is passed by a signal as represented by line 152 to block 154 which sends a signal to the prime moving means 28 or 50 which is currently being controlled to reverse direction. System control is transferred by a signal as represented by line 156+160 to block 162. In block 162 a test is made to determine whether the current value of reflected power is at a local minimum. If the current value of α is less than the value of MINIMUM then MINIMUM is updated to the current value of α and a variable COUNT is set equal to zero. If the current value of α is not less than MINIMUM then MINIMUM is not updated and the variable COUNT is set equal to COUNT+I (count=0 in Box 104, minimum is set to a large value in box 104). If count is not greater than some predetermined value, preferably 15, it is determined that there is NO local minimum and program control is passed by a signal from block 1 62 as represented by line 164 to block 158. A t block 162 if COUNT is greater than 15 then it is determined that there is a local minimum and system control is passed by a signal as represented by line 166 to block 168 which changes the control of the prime mover from 50 to 28 or from 20 to 58, thereby changing the axis which is being adjusted in order to automatically tune the cavity. From block 168 program control is passed by a signal as represented by line 170 to block 158 which executes the increments as determined in block 146 on the axis determined in blocks 162 and 168 in the direction determined in blocks 150 and 154. Program execution is then passed to block 139 which represents a return to block 130 in FIG. 6. Optionally, a signal as represented by line 172 rather than returning directly to block 138 could as represented by dash line 174 return to block 140, thereby avoiding a return to the main routine of FIG. 7 until the cavity satisfies the α condition of block 140 resulting a signal to transfer program control as represented by line 142 to block 139 for a return to block 130 of the main program in FIG. 7.

The signal output from block 130 to the autotune routine is represented by the line 131 the input signal from the autotune routine to block 130 is represented by line 176.

It will be realized that it is impossible to predict which way to change the cavity dimensions when the cavity is far from tune. However, once a resonance has been identified, a number of variations on the method above can be implemented, For example, by measuring the change in α with time, a "slope" can be generated which is less susceptible to noise than by simply comparing two individual points. It will be realized that any slope calculation requires many more computer cycles to complete compared with a simple comparison and hence there may be an impact on the response of the control program.

Another method is to place a diode detector between the launch and the power supply and measure the phase of the reflected signal. When the a cavity is in resonance, the phase moves through 180 degrees. Hence, it is possible to make decisions on the direction to move based on the phase of the signal rather than simply on the magnitude of the signal, although magnitude is used to determine the size of the step to be taken. By using phase to determine direction, there is less probability of moving in the wrong direction, although if the dielectric is changing rapidly—faster than the response of the tuning algorithm, wrong direction signals will still be encountered.

Additionally, it will be realized that the algorithms disclosed in this invention are applicable to a range of launch mechanisms in cavities and to a range of different tuning mechanisms. For example, rather than an antenna, a coupling loop can be used. A coupling loop requires adjustment in similar fashion to the antenna, with only the step size requiring optimization (as indeed the actual step size used for the antenna need some optimization for a particular cavity configuration).

Similarly, a stub and iris can also be used in place of the antenna. The iris is a fixed dimension opening and the stub (either dielectric or metallic) is preferably adjacent to the stub on the generator side of the stub. If it was possible to have an adjustable iris which would not arc at relatively high poser levels, this could be tuned using the same algorithm and the stub would not be necessary. Unfortunately, such a device has never been successfully designed.

Similarly, instead of moving the short for the cavity, by moving the sidewalls (in effect varying the diameter of the cavity) the same effect can be achieve—ie. the resonant frequency of the loaded cavity can be adjusted to match the frequency of the source. The movement of the sidewalls is difficult and only recently was a solution for that discovered. Returning to FIG. 7 system control is passed by a signal from block 130 after the call to the autotune routine as represented by line 178 to block 180 which tests if the temperature control flag has been set at block 108. If the temperature control flag is set, program control is transferred by a signal as represented by line 182 to block 184 which tests if the timer flag has been set. The timer flag is set in the interrupt subroutine. There is a test at this point to make a decision as to whether to call the temperature control routine. The data acquisition as represented by block 116 is done 20 to 30 times per second. The temperature control routine is not clone as frequently. The data acquisition and the autotune routine are contained within dashed line 186. The sequence of controls and signals within outline 186 are executed 20 to 30 times per second. If the temperature control routine were called this frequently the system would attempt to over control the temperature. The temperature control routine is preferably called from 1 to 2 times per second. Therefore, the data acquisition segment of the system represented by outline 186 is called more often. As described hereinabove the time counter is updated every $\frac{1}{18}$th of a second to call the temperature control routine twice every second the temperature control routine will be called when the time counter is evenly divisible by 9. If the time counter is easily devisable by 9, program control is transferred by a signal as represented by line 185 to block 188 which is the call to the temperature control routine. If the time counter is not evenly divisible by 9 the system control is transferred by a signal as represented by line 190 to block 192. Line 194 emanating From block 188 represents a signal for transfer of system control from block 188 to block 198 of FIG. 9.

At block 198 a test is conducted to determine whether or not the temperature is in a hold condition (referred to as a hold or soak temperature) as designated by the temperature schedule input as defined herein above. If the temperature according to the temperature schedule is in a soak condition, program control is transferred by a signal as represented by line 200 to block 202. In block 202 the current time is compared to the time at which the soak began, to determine the time already spent in the soak mode. System control is transferred from block 202 by a signal as represented by line 204 to block 206. At block 206 the current soak time is compared to the time as designated by the input temperature schedule to determine if the current soak time is greater than the desired time to be in soak as determined from the temperature time input schedule.

The soak flag is initialized to a value of zero in block 104 of FIG. 7 which represents not being in a soak. If the soak flag is equal to one it represents being in soak.

At block 206, if the current time is greater than the time desired to be in soak, programming control is transferred by a signal as represented by line 208 to block 210 in which the soak flag is reset to zero representing a condition of not being in soak. From block 210 as represented by line 212, program control is transferred by a signal to block 214. In block 214 there is a test to determine if the temperature has reached the end of the temperature time input schedule which occurs if there are no more segments of the temperature time input schedule. This can only be achieved if a final pass has been made through block 210 which resets the soak flag to off. If the temperature program is not complete, system control is transferred by a signal from block 214 as represented by line 216 to block 218 which is the return to the temperature control routine call of block 280 as represented by line 196 on FIG. 9 and FIG. 7. Since, when the program passes control from 214 via line 216 to block 218 the temperature control flag is still set to one or yes, the program control cycles through the remainder of the stream represented by block 186 of FIG. 7. This includes passing through block 180 with the temperature control flag still set to one or yes with the system control passing to block 184 as represented by line 182.

Returning to FIG. 9, if the temperature control schedule is complete, that is, there is no more data to be read from the input control schedule, the system control is passed from block 214 by a signal as represented by line 220 to block 222 which resets the end of program nag which was initialized in block 108 to be one. At block 222 of FIG. 9 the end of program flag is set to zero which is a signal for the program to stop so that when system control is transferred by a signal from block 222 as represented by line 224 to the return 218 through a signal represented by line 196 to the temperature control call 188 of FIG. 7, the system control cycles through the routine contained within dashed outline 186 of FIG. 7 and reaches block 116 by a signal represented by line 126. At block 116 the end of program flag will be zero and the program will end. Alternatively, program execution could return to, for example, block 108 to await new option settings, etc.

Returning to FIG. 9 if at block 198 the soak flag is set to zero, program control is passed by a signal as represented by line 226 to block 228. By having a single test, the program flow is simplified, e.g., if the next stage is a ramp (not soak) the program will move on after passing through block 198 (with soak=0). By looking at the initial temperature of the next input "segment" (which consists of up to one ramp and one soak) we can allow for cooling profiles and cycling, if necessary.

If the current temperature is greater than the next temperature soak, system control is transferred by a signal as represented by line 230 to block 232 which sets the soak flag equal to one or yes. System control is transferred by a signal from block 232 as represented by, line 234 to block 236. At block 236 the initial time for the beginning of the current soak is recorded—this corresponds to the time as recorded in the time counter for each pass through block 236 which only occurs when a soak in initiated. System control is transferred by a signal from block 236 as represented by line 238 to block 202. At block 202 the current time is compared to the initial time set in block 236 which is compared with the desired time in soak. The times in the temperature profile only include the soak times (set to 0 if no soak). This is the only point at which a time comparison is made and only applies for the time in soak. System control is passed by a signal from block 202 as represented by line 204 to block 206 where a test is made to determine if the time in soak is greater than the desired time. If the time in soak is greater than the desired time system control is passed by a signal from block 206 as represented by line 208 to block 210 as described herein above. If the soak time is set to zero—no soak required, program execution will move to block 210, via line 208 to reset the soak flag, as described herein above. If the current time in soak is not greater than the desired time in soak the system control is passed from block 206 by a signal as represented by line 240 to block 242 where a test is made of the current value of temperature with the desired temperature during the current segment of the temperature time schedule. If the temperature is not different than the temperature desired, the system control is passed from block 242 as represented by lines 244 and 212 to block 214. If at block 242 the temperature is different than the desired temperature, system control is passed from block 242 as represented by line 246 to block 248. At block 248 a test is made to determine if the temperature is greater than or less than the desired temperature. If the temperature is less than the desired temperature an output signal is sent from the control system to the microwave source 32 along signal line 56 from the controller 54 shown in FIG. 2. If the current temperature is higher than the desired temperature the output signal is indicative of decreasing the power output of radiation source 32. If the current temperature is lower than the desired temperature the output signal is indicative of increasing the output power of the radiation source 32. A number or temperature control algorithms could be used but the preferred method follows: the power is changed according to the following relationship:

new power=current power×desired temperature/actual temperature

System control is transferred from block 248 by a signal as represented by line 250 and 212 to block 214. The remainder of the temperature control routine will pass block 214 as described herein above.

Figure 9:
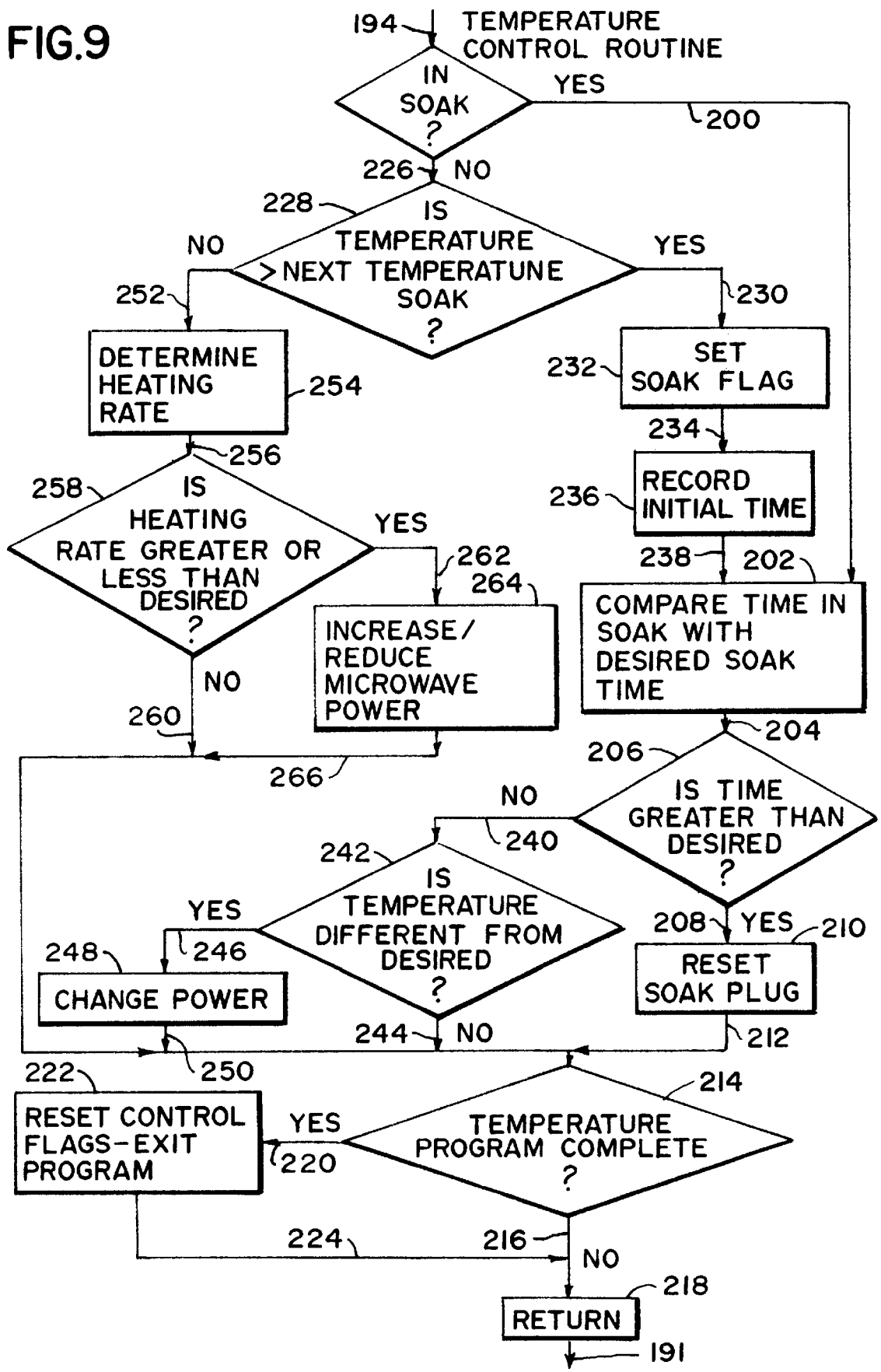
FIG. 9 is a flow chart of the temperature control subsystem of the system of FIG. 6.
Figure 10:
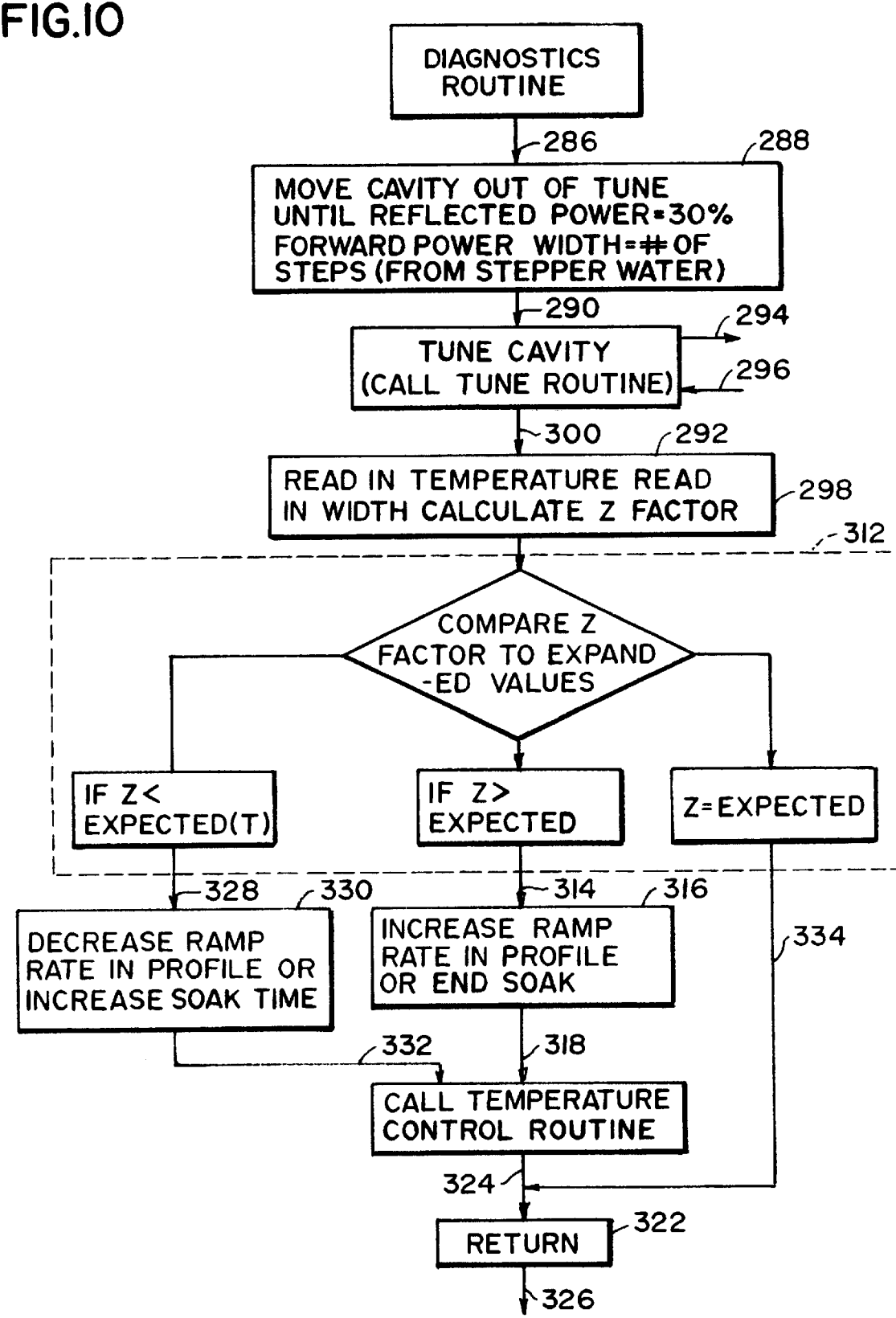
FIG. 10 is a flow chart of the diagnostic and end point detection subsystem of the system of FIG. 6.

Returning to block 228 of FIG. 9 if the current temperature is less than the next soak temperature, system control is transferred from block 228 by a signal as represented by line 252 to block 254. In block 254 a least squares linear fit is made to preferably five consecutive data points of temperature versus time to determine the heating rate. After the heating rate is determined, system control is passed by a signal as represented by line 256 to block 258. In block 258 a determination is made as to whether the heating rate is greater or less than desired. If the heating rate is not greater or less than desired, system control is passed by a signal as represented by line 260 to block 214. If the heating rate is greater or less than the desired heating rate, system control is passed from block 258 by a signal as represented by line 262 to block 264. The desired heating rate is the heating rate specified in the time/temperature schedule from the input data set as described herein above. In block 264 the power output of the radiation source 32 of FIG. 2 is increased or decreased as follows: new power is equal to the present power times the ratio of the current rate to the desired rate. An alternate method is to increment the power by a fixed amount for example 5 Watts which can be set at block 108 of FIG. 7. At block 264 a signal indicative of the increase or decrease in the current power output of radiation source 32 is controlled by a signal transmitted from controller 54 of FIG. 2 along line 56 to an input on radiation source 32 via a 0–10 V input, 10 V corresponding to fill power. The signal voltage is generated by the digital to analog section of the DAS-16 (Metrabyte) card disclosed above. The desired change in power is made at block 264 and system control is passed by a signal as represented by line 266 to block 214. The remainder of the temperature control routine from block 214 onward is described herein above.

It will be realized by one skilled in the art that a PID loop will also be able to effectively control temperature. The greatest challenge of a PID loop in a general application of this invention is that the range of heating rates are so great (from 10 C/min to 2000 C/min) in this invention that, that optimizing the parameters is extraordinarily difficult. PID loops can be relatively easily introduced if a predetermined range of heating rates is to be used for a specific product type/process. The situation is further simplified if only a "hold" temperature is required to be maintained as in the case of a continuous process where a particular zone is controlled to a predetermined temperature.

System control passes from the return block 218 of FIG. 9 of the temperature control routine by a signal as represented by the line 196 to block 188 of FIG. 7. System control is transferred by a signal from block 188 as represented by line 268 to block 192 which tests whether diagnostic flag has been set. If the diagnostic flag has not been set, system control is passed by a signal as represented by line 270 to block 124. In block 124, it is determined if the current values of the temperature, time, forward power and reflected power should be stored in memory locations and the plot on the screen set tip at block 112 updated. If this is the case, program execution transfers using line 271 to block 272 and the data of the current data points is updated on the screen set up at block 112 as described herein above. System control passes by a signal from block 272 as represented by line 274 and line 126 to block 116 at which point the program will stop if the program control flag is set to zero or off.

Returning to block 192, if the diagnostic flag is set to one, system control is passed by a signal as represented by line 276 to block 278. In block 278 there is a test to determine if the timer flag is set. Since the diagnostic routine takes a few seconds to run it is called substantially less frequently than the temperature control routine or the autotune routine. The diagnostic routine is called every five to thirty seconds. As described hereinabove when the time counter is at 18 this corresponds to one second, therefore, if the diagnostic routine is called every five seconds program control is transferred by a signal from block 278 as indicated by line 280 to block 282 when the counter has a value equal to N×5×18 where N is an integer.

If this condition is not satisfied, system control is transferred by a signal from block 278 as indicated by line 284 to block 124 and system execution from block 124 onward is as been described hereinabove. If program control is transferred to block 282 the diagnostic routine is called and the system control is transferred by a signal as indicated by line 286 to block 288 of FIG. 10. At block 288, the system sends a signal to prime mover 50 indicative of moving short 10 closer to the workpiece until the system receives ail input from meter 44 indicating that the reflected power is 30% of the signal received from meter 46. They are the minimum step size of the stepper moter. The Q of the cavity is conventionally determined from the width of the reflected power at half height. However, we have determined that a value can be obtained which is analogous to the Q by measuring the width at less than half height. The Q of the cavity then is taken as two times the distance which the short had to be moved to place it 30% out of tune. Block 288 therefore corresponds to the determination of the current value of Q. System control is transferred from block 288 by a signal as indicated by line 290 to block 292. The cavity is now tuned again by calling the tune routine. The system will cycle in the tune routine until the reflected power is less than 1% of the forward power. After the cavity has been retuned, system control is returned to block 292. System control is transferred from block 292 to the tune routine as indicated by line 294. System control returns by a signal to block 292 from the tune routine as indicated by line 296. System control is transferred from block 292 to block 298 as indicated by line 300.

Figure 12:
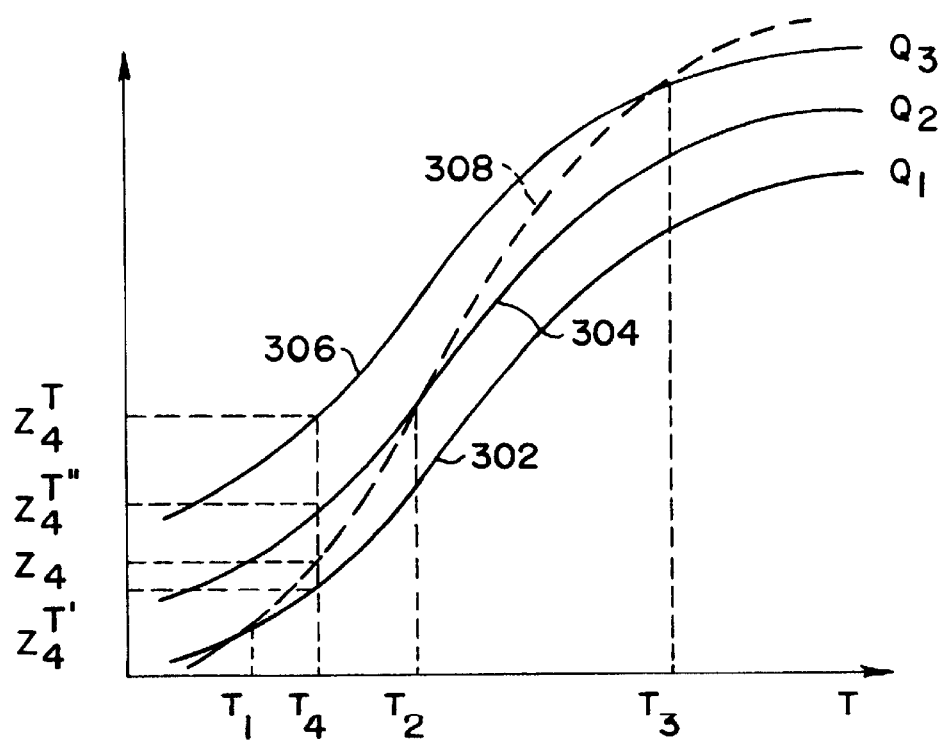
FIG. 12 shows the dependence of Q on Z and Temperature.
Figure 13:
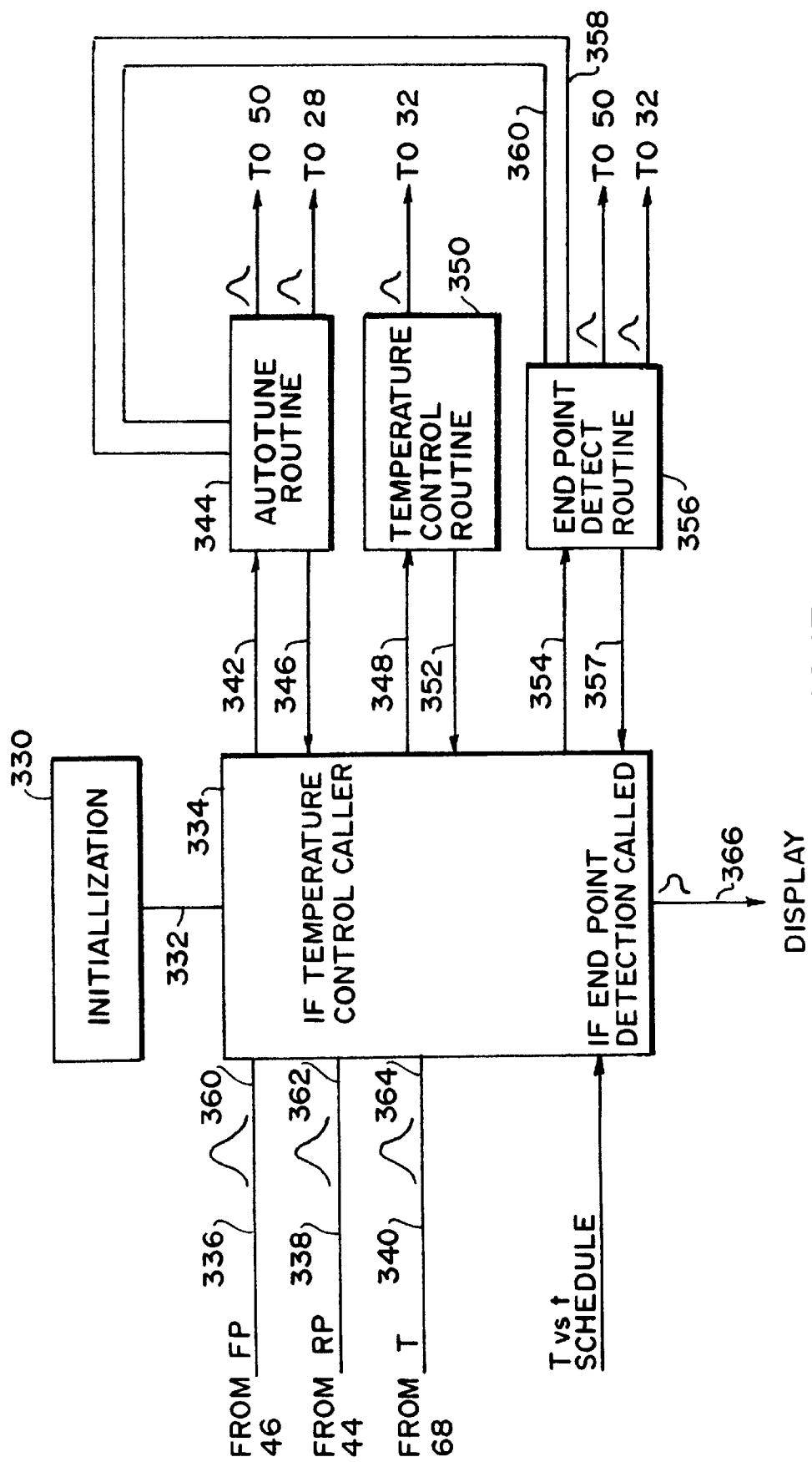
FIG. 13 is a logic block diagram showing the interconnection between subroutines for tool control.
Figure 14:
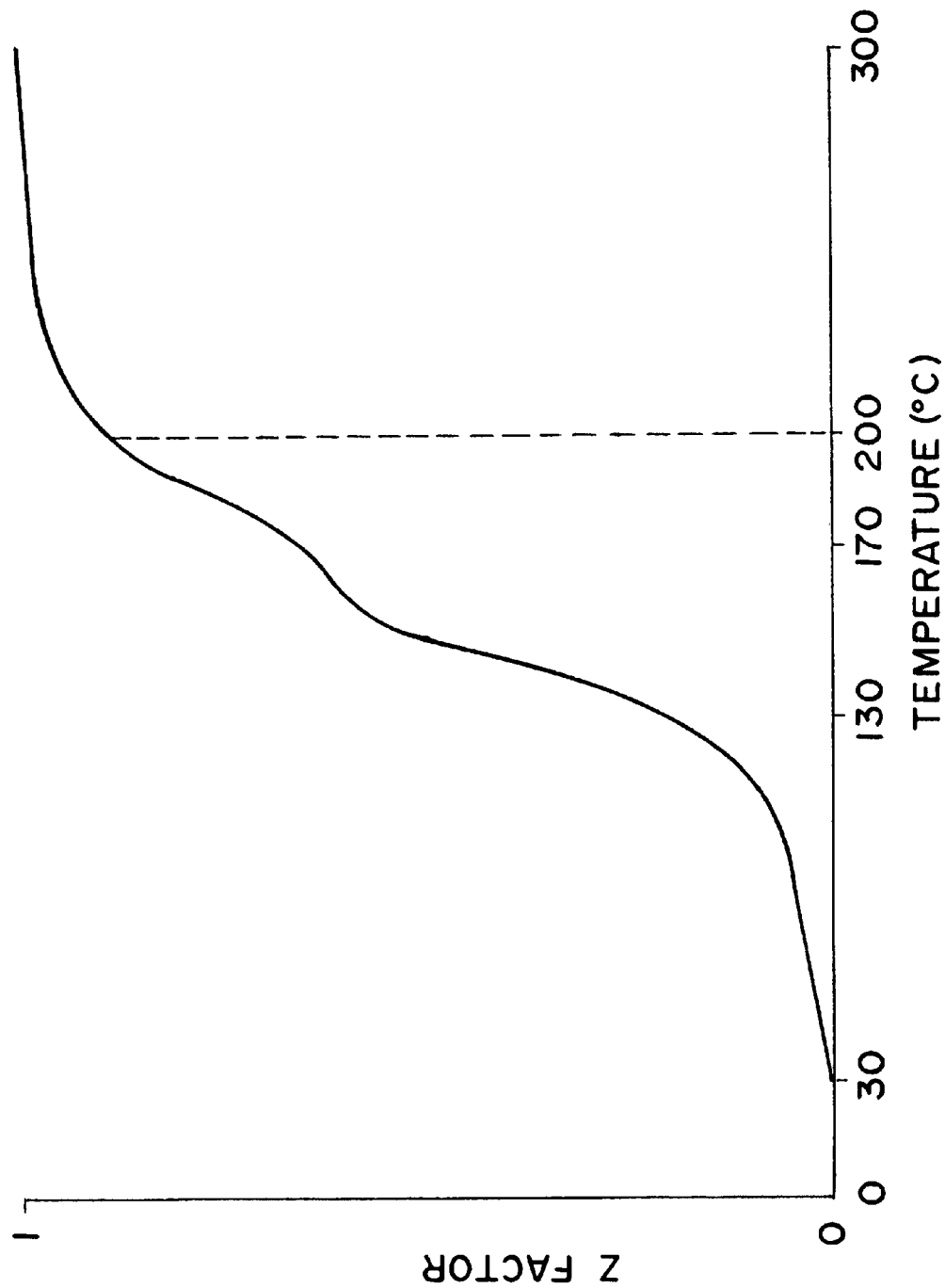
FIG. 14 is a plot of a typical Z-factor versus temperature profile as monitored during a curing process.

As described hereinabove an empirical Z factor is determined by experimental measurements. Z corresponds to the percent of cure of the sample for example, if the workpiece is a polyamic acid which is being cured to a polyimide Z corresponds to the percent cure to polyimide. The relationship between Z and Q and T can best be determined by processing the sample to a point stopping the microwave radiation to allow the sample to cool without causing further changes in the physical or chemical processes occurring during processing. During this time, Q and T are monitored (by turning the microwave on at low power for a short time). This process is then repeated and the results fitted to a curve to give Z=f(Q,T). This represents the empirical data to which an equation can be fit to determine a function wherein Z=f (Q, T) wherein f is determined by curve fitting to the data. Where it is known from an analysis of the empirical data that there are regions of the Q-T data wherein Z changes rapidly, a preferred Z versus T history can be determined. This is schematically represented in FIG. 12 by curve 308 wherein curve 308 is the Z versus T history that is preferred or the expected history which is desired to be achieved in order to most efficaciously operate on the workpiece. For example, in the case of the cure of a polyamic acid to a polyimide as described herein above, there are two regions within which Z changes rapidly as can be seen in FIG. 13 and within which it is desirable to control Z more carefully, that is, drying the solvent from the polyamic acid and curing the subsequent polyamic acid free of solvent to the polyimide. In the remainder of this discussion the expected Z refers to a generic curve of the type designated as 308 shown in FIG. 12.

At block 298 the current temperature and the current Q are used to evaluate the current Z factor. The current Z factor shall represent the Z factor which is determined from the equation or data list which is based upon empirical observations. System control is passed by a signal from block 298 as represented by line 310 to block 312. In block 312 the current Z factor is compared to the expected or desired Z factor for the current temperature. If the current Z is greater than expected, system control is passed by a signal from block 312 as represented by line 314 to block 316. Block 316 controls an output signal indicative of changing the power output of radiation source 32 by sending a signal from controller 54 along line 56, since the current Z shows that physical conditions are ahead of the expected Z. If the current segment temperature versus time profile has a temperature ramp, this ramp is increased in order to exit this segment of the temperature versus time profile more quickly, or if this segment of the temperature versus time profile is a soak condition, the soak is ended to exit this segment of the time versus temperature profile more quickly. System control is transferred by a signal from block 316 as indicated by block 318 to block 320 which is a call to the temperature control routine to continue onto the next segment of the temperature versus time profile. System control is transferred by a signal from block 320 to block 322 as indicated by line 324. Block 324 is the return to block 282 of the main routine of FIG. 7 wherein line 326 represents the return signal to the block 382.

Returning to block 312, if the current value Z is less than the expected value of Z the current physical conditions are behind the expected conditions and system control is transferred by signal from block 312 as indicated by line 328 to block 330 which sends out a signal from controller 54 along line 56 to radiation source 32 of FIG. 2 which is indicative of decreasing the ramp rate in the input profile in order to extend the time in the current segment of the temperature versus time profile or to increase to soak time in order to extend the current time spent in the soak segment of the temperature versus time profile in order to permit the current Z to come up expected value of Z. Program control is transferred from block 330 as indicated by line 332 to block 320. Progress of the system from block 320 on is described hereinabove. Returning to block 312 if the current Z is equal to the expected Z system control is transferred by a signal from block 312 as indicated by line 334 to block 322 which transfers control by a signal as indicated by line 326 to block 282 which calls the diagnostic routine. System control is transferred by a signal from block 282 as indicated by line 328 to block 272. Progress of the program after block 272 is as described hereinabove.

FIG. 13 shows a schematic diagram summarizing the control system shown in detail in FIGS. 7, 8, 9 and 10. Block 330 represents the initialization of the program which includes elements 100, 102, 104, 106, 108, 110, 112 and 114 of FIG. 7. Line 332 represents transfer of control by a signal from block 330 to block 334 which represents the data acquisition and display function of the control system. Block 334 receives a signal as indicted by line 336 indicative of the forward power, FP, from meter 46 of FIG. 2. Block 334 receives a signal as represented by line 338 from a meter 44 of FIG. 2 indicative of the reflected power. Block 334 a signal receives from temperature monitor 68 of FIG. 2 as indicated by line 340 indicative of the current temperature of the workpiece. System control is transferred by a signal from block 334 as indicated by block 342 to autotune subsystem of block 344. From the three input signals a test is determined as to whether the ratio of reflected to forward power is less than a predetermined value, preferably 0.01. If this condition is satisfied, system control is transferred by a signal back to the data acquisition and display function of block 334 as indicated by block 346. If the test of whether the cavity is in tune is not satisfied, first a signal indicative of how to move short 10 of FIG. 2 is sent to prime mover 50. If a local minimum in the reflected power is found after moving the prime mover 50, the signal indicative of how to move prime mover 28 to control the location of the antenna is provided to minimize the reflected power with respect to the antenna 22 of FIG. 2, (Movement of the antenna and short can be done in any order and can be repeated any number of times.) When a tune condition is satisfied, system control is returned by a signal from block 344 as indicated by line 346 to the central control system as represented by block 334. The central control system reads in a temperature versus time schedule. The temperature control is called, system control is transferred by a signal from block 334 as indicated by line 348 to block 350 which is the temperature control routine. If the end of the temperature versus time schedule has been reached the system control is transferred from block 350 as indicated by line 352 to the central control unit 334 and the system ends. If the end of the temperature versus time schedule has not been reached a test is made to determine if the current temperature is a temperature indicated by the temperature control schedule. If the temperature is not that is indicated by the temperature control schedule, a signal indicative of how to control the power in order to bring the temperature into agreement with the temperature control schedule is sent down line 56 to radiation control unit 32 of FIG. 2. When the current temperature is equal to the temperature as designated by the temperature versus time schedule system control is transferred by a signal from the temperature control unit 350 as indicated by line 352 to the central control unit 334. If the end point detection subsystem is desired system control is transferred by a signal from central control unit 334 as indicated by line 354 to block 356 which represents the end point detection routine. The current value of Q is determined by sending a signal along line 62 to prime mover 50 indicative of moving short 10 closer to the sample until the reflected powers is 30% of the forward power which is used to determine the value of Q. System control is transferred by a signal from block 356 as indicated by line 358 to the auto tune routine to bring the cavity back into tune. Program control is transferred back from the auto tune routine 344 to the end point detector routine 356 as indicated by line 360, The current Q value and the current T value arc used to determine the current Z value which is compared to the expected Z value. If the current Z value is equal. to the expected Z value system control is transferred by a signal from the end point detect routine of block 356 represented by line 358 to the central routine of block 334. If the current Z value is not equal to the expected Z value a signal indicative of increasing or decreasing the applied power to change the temperature ramp rate or to extend a temperature soak is sent through line 56 of FIG. 2 to radiation control unit 32. The input signals 360, 362, 364 which are indicative of forward power, reflected power, and temperature respectively are monitored $N_i$ times per second. The output signal 366 indicative of updating the display is outputted $N_d$ times per second. The autotune routine represented by block 344 is called $N_a$ times per second. The temperature control routine represented by block 350 is called $N_T$ times per second. The end point detect routine represented by block 356 is called $N_e$ times per second. The following inequality is generally applicable. $N_i<N_a<N_T<N_e$. $N_D$ is preferably one per second.

The Z factor described above can also be generated from other information. For example, the Q of the cavity is a measure of the dielectric constant of the material and that combined with temperature defines a state of the material. Hence other methods for determining dielectric constant, such as low frequency parallel plates or a dedicated microwave cavity in which either the exciting frequency is swept across a range of variables (such as if a low power signal generator is used) or by varying the dimensions of the cavity can be also be used. Also other methods such as spectroscopy (either transmission or reflection) in the UV-visible region or the IR region can be effective depending on the workpiece being processed.

In summary, the autotune subsystem basically minimizes the reflected power by: determining the state of tune—using ratio of reflected to forward power, deciding if moving closer or away for minimum (local or global); determine the direction to move motors (defaulted initially)—based on above; determining the size of step to be made—smaller closer to tune; determine if a move is necessary (not necessary if tuned); determining if the axis should be changed (due to a local minimum); and moving the short or the antenna the desired distance in the desired direction. Alternatively, the short or antenna can be swept over a relatively large range and returned to the minimum position and then move the other axis in a similar manner or move it as described above, combinations of these two approaches may be applicable—e.g. move motors stepwise until the ratio alpha starts to decrease and then go to a large swing of the motors. The size of the swing can decrease as the starting position of the movement is closer to tune.

In summary the temperature control subsystem: measures temperature, preferably surface temperature; determines the heating rate which is compared to an inputted temperature profile; and increases/decreases microwave power to obtain the appropriate heating rate or steady state temperature. The amount of change is determined by the system which controls the microwave generator preferably using an analog signal. The system stops when the heating cycle is complete (for example, by resetting flags).

In summary the end point detection subsystem: determines temperature; determines Q value, or similar for the cavity/workpiece; calculates Z factor or similar factor; compares Z factor or combination of Q and temperature with the desired profile; determines whether to end current segment (and move to next segment) or end program execution; and determines whether to extend a segment if the Z or combination of temperature and Q are not as expected. Furthermore, the end point detection system can result in previous parameters (most notably temperature) being modified to ensure that the workpiece is within predetermined specifications. This is especially the case in a continuous process in which a workpiece passes through a series of cavities in succession.

Although the invention has been described by reference to some embodiments it is not intended that the novel process and apparatus be limited thereby but that certain modifications are intended to be included as falling within the spirit and broad scope of the foregoing disclosure, the following claims and attached drawings.

What is claimed is:

1. A system for controlling the application of radiation to a workpiece in a cavity comprising:

time tracking means for tracking current times;

means for receiving a forward power signal indicative of the applied intensity of said radiation;

means for receiving a reflected power signal indicative of the reflected intensity of said radiation;

wherein a predetermined α value is determined by calculating the ratio of the forward power signal received indicative of the applied intensity of said radiation divided by the reflected power signal indicative of the reflected intensity of said radiation received, and wherein a current value of α corresponds to a current time;

means for receiving a temperature signal indicative of the temperature of said workpiece;

minimizing means for causing α to be less than a predetermined α value;

minimizing means in which α is minimizing by moving a movable launch device, said device being selected from the group consisting of a movable antenna, movable coupling loop, and a movable stub;

and a movable volume, said movable volume being selected from the group consisting of a moving short and a moving sidewall;

temperature control means for producing an intensity signal indicative of the forward power signal indicative of the applied intensity of said radiation to control said temperature to be substantially equal to a desired temperature;

means for determining the physical condition of said workpiece;

means for setting desired temperature based on current physical condition of said workpiece.

2. The system of claim 1, further including, means for producing signals corresponding to said means for receiving a forward power signal indicative of the applied intensity of said radiation, said means for receiving a reflected power signal indicative of the reflected intensity of said radiation, and said temperature, for visual display on a visual display means.

3. The system of claim 1, wherein said minimizing means produces signals corresponding to control the location of a movable volume and a movable launch device in a cavity, said system comprising:

means for receiving a signal indicative of said current value of α;

means for generating a position signal indicative of an updated location of one member of the group consisting of said launch device and said movable volume with respect to the position of said workpiece;

means for transmitting said position signal to said one member of the group consisting of said launch device and said movable volume until said current value of α is at a local minimum;

when said local minimum is reached said means for transmitting said position signal transmits said position signal to other member of the group consisting of said launch device and said movable volume; and when said current value of α is less than said predetermined α value and said current value of α is minimized.

4. The system of claim 1, wherein said temperature control means, which controls said temperature to be substantially in agreement with a predetermined temperature versus time schedule, comprises:

temperature hold determining means for producing a temperature hold signal when said temperature is to be held constant in accordance with said schedule and for producing a temperature test signal when said temperature is not to be held constant according to said schedule;

temperature test means for receiving said temperature test signal and for producing a temperature duration signal when said current temperature is greater than a next hold temperature according to said schedule and for producing a heating rate determine signal when said current temperature is not greater than said next hold temperature;

means for receiving said temperature duration signal and for producing a signal indicative of a temperature hold condition;

means for receiving said signal indicative of a temperature hold condition and for producing an initial time record signal;

means for receiving said initial time record signal and for receiving said temperature hold signal and for producing a temperature hold continue signal when said current time is in a region of said schedule indicative of holding said temperature constant and for producing a temperature hold discontinue signal when said current time is in a region of said schedule indicative of not holding said temperature constant;

means for receiving said temperature hold continue signal and for producing a temperature different than desired signal when said temperature is different than indicated by said schedule for said current time and for producing a temperature not different than desired signal when said temperature is not different than desired;

means for receiving said temperature different than desired signal and for increasing said intensity when said temperature is lower than that indicated by said schedule and for decreasing said intensity when temperature is greater than when indicated by said schedule, and for producing a temperature equal to desired signal;

means for receiving said heating rate determining signal and for determining a current heating rate and for producing a temperature rate compare signal;

means for receiving said temperature rate compare signal and for producing a temperature rate equal to expected signal when said temperature rate is substantially equal to that indicated by said schedule for said current time and for producing a temperature rate not equal to expected signal when said temperature rate is not equal to that indicated by said schedule for said current time;

means for receiving said temperature rate not equal to expected signal and for producing a signal indicative of increasing said intensity when said heating rate is less than indicated by said schedule for said current time and for producing a signal indicative of decreasing said intensity when said heating rate is greater than indicated by said schedule for said current time and for producing a second temperature rate equal to expected signal when said temperature rate is substantially equal to said rate indicated by said schedule for said current time; and means for determining when said current time is substantially equal to an end time of said schedule and for receiving said temperature equal to desired signal and for receiving said temperature not different than desired signal and for receiving said temperature hold discontinue signal and for producing a schedule end signal when said current time is not less than said end time and for producing a schedule not ended signal when said current time less than said end time.

5. The system of claim 1, in a cavity wherein said means for determining when said workpiece has achieved a final predetermined physical condition comprises:

resonant generating means in said cavity for generating a signal representative of a current Q value, said Q value being the ratio of the measure of energy stored in the cavity divided by the average power lost therein;

means for executing said minimizing means to return said α value to a minimum;

means for determining from said current Q value and said current temperature whether said workpiece has achieved said predetermined physical condition.

6. The system of claim 5, wherein said resonant generating means generates a signal to place said α value in a nonminimized condition to determine said current Q value for said workpiece.

7. The system of claim 6, wherein said $\alpha$ value in said nonminimized condition is at a value of about 0.3.

8. A system for controlling the application of radiation to a workpiece in a cavity comprising:

time tracking means for tracking current time;

means for receiving a forward power signal indicative of the applied intensity of said radiation;

means for receiving a reflected power signal indicative of the reflected intensity of said radiation;

wherein a predetermined $\alpha$ value is determined by calculating the ratio of the received forward power signal indicative of the applied intensity of said radiation divided by the received reflected power signal indicative of the reflected intensity of said radiation, and wherein a current value of $\alpha$ corresponds to said current time;

means for receiving a temperature signal indicative of the temperature of said workpiece;

$\alpha$ minimizing means for causing a to be less than a predetermined $\alpha$ value;

means for producing an intensity signal indicative for each the reflected intensity and the applied intensity of said radiation to control said temperature to be substantially equal to a predetermined temperature;

means for determining when said workpiece has achieved a final predetermined physical condition; and means for producing a signal indicative of whether said workpiece has achieved said final predetermined physical condition;

means to vary said predetermined temperature to achieve predetermined physical condition; said $\alpha$ minimizing means which produces signals to control the location of a launch device and a variable volume device, comprises:

means for receiving a signal indicative of said current value of $\alpha$;

means for generating a position signal indicative of an updated location of one member of the group consisting of said launch device and said variable volume device with respect to the position of said workpiece;

means for transmitting said position signal to said one member of the group consisting of said launch device and said variable volume until said current value of $\alpha$ is at a local minimum;

when said local minimum is reached, said means for transmitting said position signal transmits said position signal to the other member of the group consisting of said launch device and said variable volume device;

wherein said launch device is in said cavity and is selected from the group consisting of a movable antenna, a movable coupling loop, and a movable stub;

wherein said variable volume device is achieved by one of the group consisting of a moving short, and a moving sidewall; and when said current value of $\alpha$ is less than said predetermined $\alpha$ value, said current value of $\alpha$ is minimized;

temperature control means, which controls said temperature to be substantially in agreement with a predetermined temperature versus time schedule, comprises:

temperature hold determining means for producing a temperature hold signal when said temperature is to be held constant in accordance with said schedule and for producing a temperature test signal when said temperature is not to be held constant according to said schedule;

temperature test means for receiving said temperature test signal and for producing a temperature duration signal when said temperature is greater than a next hold temperature according to said schedule and for producing a heating rate determine signal when said temperature is not greater than said next hold temperature;

means for receiving said temperature duration signal and for producing a signal indicative of a temperature hold condition;

means for receiving said signal indicative of a temperature hold condition and for producing an initial time record signal;

means for receiving said initial time record signal and for receiving said temperature hold signal and for producing a temperature hold continue signal when said current time is in a region of said schedule indicative of holding said temperature constant and for producing a temperature hold discontinue signal when said current time is in a region of said schedule indicative of not holding said temperature constant;

means for receiving said temperature hold continue signal and for producing a temperature different than desired signal when said temperature is different than indicated by said schedule for said current time and for producing a temperature not different than desired signal when said temperature is not different than desired;

means for receiving said temperature different than desired signal and for increasing said applied intensity when said temperature is lower than that indicated by said schedule and for decreasing said intensity when said temperature is greater than when indicated by said schedule, and for producing a temperature equal to desired signal;

means for receiving said heating rate determining signal and for determining a current heating rate and for producing a temperature rate compare signal, means for receiving said temperature rate compare signal and for producing a temperature rate equal to expected signal when said temperature rate is substantially equal to that indicated by said schedule for said current time and for producing a temperature rate not equal to expected signal when said temperature rate is not equal to that indicated by said schedule for said current time;

means for receiving said temperature rate not equal to expected signal and for producing a signal indicative of increasing said intensity when said heating rate is less than indicated by said schedule for said current time and for producing a signal indicative of decreasing said intensity when said heating rate is greater than indicated by said schedule for said current time and for producing a second temperature rate equal to expected signal when said temperature rate is substantially equal to said rate indicated by said schedule for said current time; and means for determining when said current time is substantially equal to an end time of said schedule and for receiving said temperature equal to desired signal and for receiving said temperature not different than desired signal and for receiving said temperature hold discontinue signal and for producing a schedule end signal when said current time is not less than said end time and for producing a schedule not ended signal when said current time less than said end time;

said means for determining when said workpiece has achieved a final predetermined physical condition comprises:

means for generating a signal to place said $\alpha$ value in a nonminimized condition to determine a current Q value for said workpiece, wherein Q value is the ratio of the measure of energy stored in said cavity divided by the average power loss therein;

means for executing said $\alpha$ minimizing means to return said $\alpha$ value to a minimum;

means for determining from said current Q value and said current temperature whether said workpiece has achieved said predetermined physical condition.

9. The system of claim 1, wherein said $\alpha$ minimizing means comprises:

means for generating a signal to modify said cavity to vary said current value of $\alpha$;

means for determining in response to said varying said current value of $\alpha$ if said current value of $\alpha$ is increasing or decreasing; and means for generating a signal in response to said determination of whether said current value of $\alpha$ is increasing or decreasing, for modifying said cavity to minimize said current value of $\alpha$.

10. The system of claim 1, wherein said temperature control means comprises:

means for receiving specific temperature values of said temperature signal corresponding to specific time values of said current time;

means for producing a heating rate signal in response to determining a heating rate from said specific temperature value and said specific time values;

means for producing a comparison signal in response to determining a heating rate from said specific temperature values and said specific time values;

means for producing a comparison signal in response to comparing said heating rate signal with a predetermined temperature versus time schedule; and means for producing a signal to modify said forward power in response to said comparison signal.

11. The system of claim 1, wherein said means for determining when said workpiece has achieved a final predetermined physical condition comprises:

means for determining a current Q for said cavity; and means for comparing said current Q and said temperature with a predetermined Q, temperature versus degrees of workpiece physical condition schedule, wherein Q value is the ratio of the measure of energy stored in said cavity divided by the average power loss therein.

12. A method for controlling the application of radiation to a workpiece in a cavity comprising:

tracking current times;

measuring a forward radiation intensity applied to said workpiece at said current time;

measuring a reflected intensity reflected from said workpiece at said current time;

determining a predetermined $\alpha$ value by calculating the ratio of the forward radiation intensity divided by the reflected intensity of said radiation and wherein a current value of $\alpha$ corresponds to a current time;

employing means to minimize $\alpha$;

wherein said $\alpha$ minimizing means includes varying the position of a movable launch device in said cavity, said device is selected from the group consisting of a movable antenna, movable coupling loop, and a movable stub;

and varying the position of a movable volume device, said movable volume device being selected from the group consisting of a moving short and a moving sidewall;

measuring a temperature of said workpiece at said current time;

controlling said measured temperature to be substantially equal to a predetermined temperature;

determining whether said workpiece has achieved a final predetermined physical condition; and adjusting said forward radiation intensity if said workpiece has not achieved said final predetermined physical condition.

13. The method of claim 12, further including producing and displaying on a visual display signals corresponding to said forward intensity, said reflected intensity and said temperature.

14. The method of claim 12, wherein said step of minimizing $\alpha$ is achieved by controlling the location of said a launch device and said volume device in said cavity by a method comprising:

determining said current value of $\alpha$;

moving to an updated location one member of the group consisting of said launch device and said volume device with respect to the position of said workpiece until a local minimum in said current value of $\alpha$ is achieved; and when said local minimum is achieved moving the other member of said group consisting of said volume device and said launch device until said current value of $\alpha$ is less than a predetermined value of $\alpha$.

15. The method of claim 12 wherein said measured temperature is controlled to be substantially equal to a predetermined temperature indicated by a temperature versus time schedule, by a method comprising:

comparing said measured temperature to said schedule;

determining if at said current time according to said schedule if said measured temperature is to be held constant;

determining if at said current time according to said schedule if said measured temperature is not to be held constant;

if said measured temperature is to be held constant determining when according to said schedule to change said temperature;

if said measured temperature is not to be held constant determining according to said schedule a current heating rate;

increasing said forward intensity if said measured temperature is less than that indicated by said schedule for said current time;

decreasing said forward intensity if said measured temperature is greater than that indicated by said schedule for said current time;

determining when said current time is equal to an end time of said schedule.

16. The method of claim 12, wherein said step of determining when said workpiece has achieved a final predetermined physical condition comprises:

moving the position of one of the group of said antenna and said short to place said $\alpha$ value at a minimum condition, determining at said nonminimum condition a current Q value for said workpiece;

returning said current $\alpha$ value to a minimum, determining from said current Q value and said measured temperature whether said workpiece has achieved said predetermined physical condition, wherein Q value is the ratio of the measure of energy stored in said cavity divided by the average power loss therein.

17. The system of claim 8, wherein said means for determining when said workpiece has achieved a final predetermined physical condition is selected from the group comprising:

measuring dielectric properties of said workpiece, measuring degree of conversion of said workpiece, measuring residual solvent content, measuring residual moisture content.

18. The method of claim 16, wherein said $\alpha$ value in said nonminimum condition is at a value of about 0.3.

19. The method of claim 12, wherein said step of minimizing $\alpha$ comprises:

modifying said cavity to vary said current value of $\alpha$;

determining in response to said varying said current value of $\alpha$ if said current value of $\alpha$ is increasing or decreasing; and modifying said cavity to minimize said current value of $\alpha$.

20. The method of claim 12, wherein said step of controlling said measured temperature comprises:

monitoring specific temperature values corresponding to specific time values;

determining a heating rate from said specific temperature values and said specific time values;

comparing said heating rate with a predetermined temperature versus time schedule; and modifying said forward intensity in response to said comparing.

21. The method of claim 12, wherein said step of controlling said measured temperature comprises:

monitoring specific temperature values corresponding to specific time values;

comparing said measured temperature with a predetermined temperature; and modifyng said forward intensity in response to said comparing.

22. The method of claim 12, wherein said step of determining when said workpiece has achieved a final predetermined physical condition comprises:

determining a current Q for said cavity; and comparing said current Q and said measured temperature with a predetermined Q, and temperature versus degree of workpiece physical condition schedule, wherein Q value is the ratio of the measure of energy stored in said cavity divided by the average power loss therein.

23. The system of claim 8, wherein said means for determining when said workpiece has achieved a final predetermined physical condition is selected from the group comprising:

measuring dielectric properties of said workpiece, measuring degree of conversion of said workpiece, measuring residual solvent content, measuring residual moisture content.

24. A system for controlling an application of radiation to a workpiece in a cavity comprising:

time tracking means for tracking current time;

means for receiving an applied power signal indicative of a magnitude of an applied intensity of said radiation;

means for receiving a reflected power signal indicative of a magnitude of a reflected intensity of said radiation;

means for receiving a phase signal indicative of the phase of the said radiation means for receiving a temperature signal indicative of a magnitude of a temperature of said workpiece;

minimizing means coupled to said time tracking means, for causing $\alpha$ to be less than a predetermined value, $\alpha$ is a ratio of said magnitude of said reflected intensity over said magnitude of said applied intensity and coupled to said phase signal to provide a signal corresponding to signal a current value of $\alpha$ signal corresponding to said current time;

said minimizing means being coupled to said time tracking means, to said means for receiving said applied power signal indicative of said magnitude of said applied intensity, to said means for receiving said reflected power signal indicative of said magnitude of said reflected intensity and to said means for receiving said temperature signal indicative of said magnitude of said temperature of said workpiece;

temperature control means coupled to said time tracking means, for producing an intensity signal indicative of said magnitude of said applied intensity of said radiation to control said temperature of said workpiece to be substantially equal to a predetermined temperature;

means for determining when said workpiece has achieved a final predetermined physical condition; said means for determining is coupled to said time tracking means; and means for producing an end signal to end operation of said system when said workpiece has achieved said final predetermined physical condition; said means for producing is coupled to said time tracking means.

25. A system for controlling an application of radiation to a workpiece in a cavity comprising:

time tracking means for tracking current time;

means for receiving an applied power signal indicative of a magnitude of an applied intensity of said radiation;

means for receiving a reflected power signal indicative of a magnitude of a reflected intensity of said radiation;

means for receiving a temperature signal indicative of a magnitude of a temperature of said workpiece;

minimizing means coupled to said time tracking means, for causing $\alpha$ to be less than a predetermined value, $\alpha$ is a ratio of said magnitude of said reflected intensity over said magnitude of said applied intensity and to provide a signal corresponding to signal a current value of $\alpha$ signal corresponding to said current time;

said minimizing means being coupled to said time tracking means, to said means for receiving said applied power signal indicative of said magnitude of said applied intensity, to said means for receiving said reflected power signal indicative of said magnitude of said reflected intensity and to said means for receiving said temperature signal indicative of said magnitude of said temperature of said workpiece;

said minimizing means is achieved by moving a movable volume element and a movable launch device;

where said movable launch device in said cavity is selected from the group consisting of a movable antenna, movable coupling loop, movable stub and;

where said movable volume is achieved by one of the group of a moving short, a moving sidewall;

temperature control means coupled to said time tracking means, for producing an intensity signal indicative of said magnitude of said applied intensity of said radiation to control said temperature of said workpiece to be substantially equal to a predetermined temperature;

means for determining when said workpiece has achieved a final predetermined physical condition; said means for determining is coupled to said time tracking means; and means for producing a signal to control said predetermined temperature if said workpiece has not achieved said final predetermined physical condition; said means for producing is coupled to said time tracking means.

26. The system of claim 25, wherein said cavity further includes a short and an antenna and wherein said minimizing means produces signals to control a location of said short and said antenna in said cavity comprising:

means for receiving said current value of $\alpha$ signal;

means for generating a position signal indicative of an updated location of one member of the group consisting of said antenna and said short with respect to the position of said workpiece;

means for transmitting said position signal indicative of said updated location to said one member of the group consisting of said antenna and said short until said current value of $\alpha$ is at a local minimum;

when said local minimum is reached, said means for transmitting said position signal indicative of said updated location transmits said position signal indicative of said updated location to the other member of said group consisting of said movable volume element and said movable launch device; and when said current value of $\alpha$ is less than said predetermined value, said current value of $\alpha$ is minimized.

27. A system for controlling an application of radiation to a workpiece having a position in a cavity comprising:

time tracking means for tracking current time;

means for receiving a forward power signal indicative of a magnitude of an applied intensity of said radiation;

means for receiving a reflected power signal indicative of a magnitude of a reflected intensity of said radiation;

means for receiving a temperature signal indicative of a magnitude of a temperature of said workpiece;

minimizing means for causing $\alpha$ to be less than a predetermined a value, wherein $\alpha$ is a ratio of said magnitude of said reflected intensity over said magnitude of said applied intensity and wherein a current value of a corresponding to said current time;

said minimizing means being coupled to said timetracking means, to said means for receiving said applied power signal indicative of said magnitude of said applied intensity, to said means for receiving said reflected power signal indicative of said magnitude of said reflected intensity and to said means for receiving said temperature signal indicative of said magnitude of said temperature of said workpiece;

wherein said minimizing means is accomplished by moving movable volume element and movable launch device;

means for producing an intensity signal indicative of an intensity of said radiation to control said temperature to be substantially equal to a predetermined temperature;

means for determining when said workpiece has achieved a final predetermined physical condition; and means for producing a signal to control said predetermined temperature if said workpiece has not achieved said final predetermined physical condition;

said minimizing means which produces signals to control a location of a short and an antenna in said cavity comprises:

means for receiving a signal indicative of a current value of $\alpha$;

means for generating a position signal indicative of an updated location of one member of the group consisting of said antenna and said short with respect to a position of said workpiece, said one member being a selected member and the other member being an unselected member;

means for transmitting said position signal indicative of an updated location to said one member of the group consisting of said antenna and said short until said current value of $\alpha$ is at a local minimum;

when said local minimum is reached, said means for transmitting said position signal indicative of an updated location transmits said position signal indicative of an updated location to said unselected member of the group consisting of said movable sidewall and said movable launch device, selected from the group consisting of a movable stub, movable coupling loop and movable antenna;

when said current value of $\alpha$ is less than said predetermined a value, said current value of $\alpha$ is minimized;

a temperature control means, which controls a temperature to be substantially in agreement with a predetermined temperature versus time schedule, comprises:

temperature hold determining means for producing a temperature hold signal when said temperature is to be held constant in accordance with said schedule and for producing a temperature test signal when said temperature is not to be held constant according to said schedule;

temperature test means for receiving said temperature test signal and for producing a temperature duration signal when said temperature is greater than a next hold temperature according to said schedule and for producing a heating rate determine signal when said temperature is not greater than said next hold temperature;

means for receiving said temperature duration signal and for producing a signal indicative of a temperature hold condition;

means for receiving said signal indicative of a temperature hold condition and for producing an initial time record signal;

for receiving said initial time record signal and for receiving said temperature hold signal and for producing a temperature hold continue signal when said current time is in a region of said schedule indicative of holding said temperature constant and for producing a temperature hold discontinue signal when said time is in a region of a schedule indicative of not holding said temperature constant;

means for receiving said temperature hold continue signal and for producing a temperature different than desired signal when said temperature is different than indicated by said schedule for said time and for producing a temperature not different than desired signal when said temperature is not different than desired;

means for receiving said temperature different than desired signal and for increasing said applied intensity when said temperature is lower than that indicated by said schedule indicative of not holding said temperature constant and for decreasing said intensity when said temperature is greater than when indicated by said schedule; indicative of not holding said temperature constant, and for producing a temperature equal to desired signal;

means for receiving said heating rate determining signal and for determining a current heating rate and for producing a temperature rate compare signal, means for receiving said temperature rate compare signal and for producing a temperature rate equal to expected signal when said temperature rate is substantially equal to that indicated by said schedule for said current time and for producing a temperature rate not equal to expected signal when said temperature rate is not equal to that indicated by said schedule for said current time;

means for receiving said temperature rate not equal to expected signal and for producing a signal indicative of increasing said intensify when said heating rate is less than indicated by said schedule for said current time and for producing a signal indicative of decreasing said intensity when said heating rate is greater than indicated by said schedule for said current time and for producing a second temperature rate equal to expected signal when said temperature rate is substantially equal to said rate indicated by said schedule for sad time; and means for determining when said current time is substantially equal to an end time of said schedule and for receiving said temperature equal to desired signal and for receiving said temperature not different than desired signal and for receiving said temperature hold discontinue signal and for producing a schedule end signal when said current time is not less than said end time and for producing a schedule not ended signal when said current time less than said end time;

said means for determining when said workpiece has achieved a final predetermined physical condition comprises:
  means for generating a signal to place said a value in a nonminimized condition to determine a current Q value for said workpiece;
  means for executing said a minimizing means to return said a value to a minimum;
  means for determining from said current Q value and said current temperature whether said workpiece has achieved said predetermined physical condition wherein said Q is the ratio of energy stored to energy lost in said cavity.

28. A system for controlling an application or radiation to a workpiece in a cavity comprising:

time tracking means for tracking current time;

means for receiving an applied power signal indicative of the applied intensity of said radiation;

means for receiving a reflected power signal indicative of a magnitude of a reflected intensity of said radiation;

means for receiving a temperature signal indicative of a magnitude of a temperature of said workpiece;

a minimizing means coupled to said time tracking means for causing α to be less than a predetermined value, wherein α is a ratio of said magnitude of said reflected intensity over said magnitude of said applied intensity;

said minimizing means being coupled to said timetrack aid means for receiving said applied power signal indicative of said magnitude of said applied intensity, to said means for receiving said reflected power signal indicative of said magnitude of said reflected intensity and to said means for receiving said temperature signal indicative of said magnitude of said temperature of said workpiece;

temperature control means for producing an intensity signal indicative of a magnitude of an intensity of said radiation to control said temperature to be substantially equal to a predetermined temperature from a predetermined temperature versus time schedule;

means for determined when said workpiece has achieved a final predetermined physical condition, said means for determining is operatively connected to said time tracking means;

means for producing a signal to modify said predetermined temperature if said workpiece has not achieved said final predetermined physical condition, said means for producing is operatively connected to said time tracking means;

said minimizing means comprises:
  means for generating a signal to modify said cavity to vary a value of α;
  means for determining in response to said varying said value of α if said value of α is increasing or decreasing; and
  means for generating a signal in response to a determination of whether said current value of α is increasing or decreasing, for modifying said cavity to minimize said current value of α;
  means for varying position of variable launch device, selected from the group movable coupling loop and movable stub and movable volume element selected from the group consisting of a movable sidewall and a movable short;

said temperature control means comprises:
  means for receiving specific temperature values of said temperature signal corresponding to specific time values of said current time;
  means for producing a heating rate signal in response to determining a heating rate from said specific temperature values and said specific time values;
  means for producing a comparison signal in response to comparing said heating rate signal with said predetermined temperature versus time schedule; and
  means for producing a signal to modify said applied power signal indicative of the applied intensity in response to said comparison signal;

said means for determining when said workpiece has achieved a final predetermined physical condition comprises:
  means for determining a current Q for said cavity wherein said current Q; and
  means for comparing said current Q and said current temperature with a predetermined Q, and temperature versus degree of workpiece physical condition schedule wherein said Q is the ratio of energy stored to energy lost in said cavity.

29. A method for controlling the application of radiation to a workpiece in a cavity comprising:

tracking current time;

measuring a forward radiation intensity applied to said workpiece at said current time;

measuring a reflected radiation intensity reflected from said workpiece at said current time;

minimizing $\alpha$ wherein $\alpha$ is a ratio of said magnitude of said reflected intensity over said magnitude of said applied intensity and wherein a current value of $\alpha$ corresponds to said current time;

minimizing $\alpha$ by sequentially moving one of the group a variable volume element or a variable wherein the said movable volume element comprises a movable sidewall and the said variable launch device comprises one selected from the group comprising a movable antenna, a movable coupling loop and a movable stub;

measuring a temperature of said workpiece at said current time;

controlling a current temperature to be substantially equal to a predetermined temperature;

determining when said workpiece has achieved a final predetermined physical condition; and stopping said applied intensity when said workpiece has achieved said final predetermined physical condition.

30. An apparatus for controllably applying radiation to a workpiece comprising:

a tunable cavity comprising a means for adjusting the resonant frequency and impedance match of said cavity;

a means for providing applied power having an applied intensity;

a means for measuring said applied intensity;

a means for measuring a reflected power reflected from said workpiece, said reflected power having a reflected intensity;

a means for measuring a temperature of said workpiece;

a means for minimizing a ratio of said magnitude of said reflected intensity over said applied intensity;

a time tracking means for tracking current time;

said means for minimizing being operatively connected to said time tracking means to provide a current value of said ratio corresponding to said current time;

temperature control means operatively connected to said time tracking means for producing an intensity signal indicative of said magnitude of said applied intensity of said radiation to control said temperature of said workpiece to be substantially equal to a predetermined temperature;

means for determining when said workpiece has achieved a final predetermined physical condition;

means for producing an end signal to end operation of said apparatus when said workpiece has achieved said final predetermined physical condition; and wherein said means for adjusting the resonant frequency and impedance match of said cavity comprises moving a movable short, a sidewall a movable coupling loop, an adjustable iris, a movable stub and a movable antenna.

31. A method of controllably applying radiation to a workpiece in a tunable cavity comprising a means for adjusting the resonant frequency of said cavity comprising:

wherein said tunable cavity comprises a movable parameters selected from the group a movable short, a sidewall a movable stub, a movable iris, a movable coupling loop and a movable antenna;

providing applied power having an applied intensity;

measuring said applied intensity;

measuring a reflected power reflected from said workpiece, said reflected power having a reflected intensity;

measuring a temperature of said workpiece;

minimizing a ratio of said magnitude of said reflected intensity over said applied intensity;

tracking current time;

a current value of said ratio corresponding to said current time;

controlling said magnitude of said applied intensity of said radiation to control said temperature of said workpiece to substantially equal to a predetermined value;

determining when said workpiece has achieved a final predetermined physical condition; and stopping said applied power when said workpiece has achieved said final predetermined physical condition.

\* \* \* \* \*